United States Patent [19]
Chandler

[11] Patent Number: 6,017,767
[45] Date of Patent: *Jan. 25, 2000

[54] ASSAY DEVICE

[75] Inventor: Howard M. Chandler, West Vancouver, Canada

[73] Assignee: Beckman Coulter, Inc., Fullerton, Calif.

[*] Notice: This patent is subject to a terminal disclaimer.

[21] Appl. No.: 08/465,428

[22] Filed: Jun. 5, 1995

Related U.S. Application Data

[62] Division of application No. 08/194,793, Feb. 10, 1994, which is a continuation of application No. 07/888,831, May 27, 1992, abandoned, which is a continuation-in-part of application No. 07/706,639, May 29, 1991.

[51] Int. Cl.[7] ........................ G01N 33/558; G01N 33/543
[52] U.S. Cl. .............................. 436/514; 422/56; 422/57; 422/58; 422/61; 435/7.1; 435/7.2; 435/7.9; 435/7.93; 435/7.94; 435/7.95; 435/287.7; 435/287.9; 435/288.4; 435/288.5; 435/969; 435/970; 435/973; 436/518; 436/524; 436/807; 436/809; 436/810
[58] Field of Search .................................. 422/56, 57, 58, 422/61, 99; 435/7.1, 7.2, 7.9, 7.93, 7.94, 7.95, 287.7, 287.9, 288.4, 288.5, 969, 970, 973; 436/518, 514, 524, 807, 809, 810

[56] References Cited

U.S. PATENT DOCUMENTS

| Re. 30,267 | 5/1980 | Bruschi . |
|---|---|---|
| Re. 31,006 | 8/1982 | Schuurs et al. . |
| 1,926,299 | 9/1933 | Monk . |
| 3,078,031 | 2/1963 | Kauffeld . |
| 3,186,623 | 6/1965 | Guyer . |

(List continued on next page.)

FOREIGN PATENT DOCUMENTS

| 0045476 | 2/1982 | European Pat. Off. . |
|---|---|---|
| 0063810 | 11/1982 | European Pat. Off. . |
| 0088636 | 9/1983 | European Pat. Off. . |
| 0125118 | 11/1984 | European Pat. Off. . |
| 0154749 | 9/1985 | European Pat. Off. . |

(List continued on next page.)

OTHER PUBLICATIONS

Wilchek, et al., "The Avidin–Biotin Complex in Immunology", Immunology Today (1984), vol. 5, No. 2, pp. 39–43.
Copy of International Search Report for corresponding PCT application serial no. US96/07576 filed on May 23, 1996.

*Primary Examiner*—Christopher L. Chin
*Assistant Examiner*—Bao-Thuy L. Nguyen
*Attorney, Agent, or Firm*—William H. May; Margaret A. Kivinski; Merchant & Gould

[57] ABSTRACT

A chromatographic assay device for use with immunoassays allows rapid and convenient assays of analytes of biological interest, and permits extractions to be carried out in situ, avoiding the use of separate extraction vessels. The device has a wide dynamic range and avoids interference from particulates or colored components. In one form, the device comprises: (1) a first opposable component comprising a sample preparation means adapted to receive a sample to be assayed; and (2) a second opposable component comprising a chromatographic medium. The first and second opposable components can be brought into opposition so as to cause the sample preparation means to apply the sample to be tested to the chromatographic medium. Preferably, the analyte is detected with a visually detectable label. Other variations of the device vary the arrangement of components to provide optimal chromatography for a variety of analytes, as well as to permit bidirectional chromatography. The devices can be incorporated in test kits, and assay methods using the devices are also disclosed.

15 Claims, 6 Drawing Sheets

U.S. PATENT DOCUMENTS

| | | |
|---|---|---|
| 3,307,770 | 3/1967 | Wysocki . |
| 3,420,205 | 1/1969 | Morison . |
| 3,437,449 | 4/1969 | Luckey . |
| 3,475,129 | 10/1969 | Peurifoy . |
| 3,551,555 | 12/1970 | Schuurs . |
| 3,720,760 | 3/1973 | Bennich et al. . |
| 3,723,064 | 3/1973 | Liotta . |
| 3,798,004 | 3/1974 | Zerachia et al. . |
| 3,811,840 | 5/1974 | Bauer et al. . |
| 3,867,517 | 2/1975 | Ling . |
| 3,888,629 | 6/1975 | Bagshawe . |
| 3,893,808 | 7/1975 | Campbell . |
| 3,901,657 | 8/1975 | Lightfoot . |
| 3,902,964 | 9/1975 | Greenspan . |
| 3,915,647 | 10/1975 | Wright . |
| 3,926,564 | 12/1975 | Giaever . |
| 3,932,220 | 1/1976 | Liotta . |
| 3,933,594 | 1/1976 | Milligan et al. . |
| 3,933,997 | 1/1976 | Hersh et al. . |
| 3,935,074 | 1/1976 | Rubenstein et al. . |
| 3,949,064 | 4/1976 | Bornstein et al. . |
| 3,951,332 | 4/1976 | Torbeck . |
| 3,960,499 | 6/1976 | White . |
| 3,961,894 | 6/1976 | Gordon . |
| 3,966,897 | 6/1976 | Renn et al. . |
| 3,975,162 | 8/1976 | Renn et al. . |
| 3,979,509 | 9/1976 | Giaever . |
| 3,981,981 | 9/1976 | Reunanen . |
| 3,984,533 | 10/1976 | Uzgiris . |
| 3,985,867 | 10/1976 | Redshaw . |
| 3,989,591 | 11/1976 | Liotta . |
| 3,992,158 | 11/1976 | Przybylowicz . |
| 3,993,451 | 11/1976 | Verbeck . |
| 3,996,006 | 12/1976 | Pagano . |
| 4,012,198 | 3/1977 | Finter et al. . |
| 4,016,043 | 4/1977 | Schuurs . |
| 4,017,597 | 4/1977 | Reynolds . |
| 4,018,662 | 4/1977 | Ruhenstroth-Bauer et al. . |
| 4,020,151 | 4/1977 | Bolz et al. . |
| 4,038,485 | 7/1977 | Johnston et al. . |
| 4,039,652 | 8/1977 | Adams et al. . |
| 4,042,335 | 8/1977 | Clement . |
| 4,046,514 | 9/1977 | Johnston et al. . |
| 4,053,284 | 10/1977 | Posch . |
| 4,054,646 | 10/1977 | Giaever . |
| 4,059,407 | 11/1977 | Hochstrasser . |
| 4,065,383 | 12/1977 | Skare et al. . |
| 4,066,403 | 1/1978 | Bruschi . |
| 4,067,774 | 1/1978 | Rubenstein et al. . |
| 4,067,959 | 1/1978 | Bolz . |
| 4,087,326 | 5/1978 | Kereluk . |
| 4,087,332 | 5/1978 | Hansen . |
| 4,094,647 | 6/1978 | Deutsch et al. . |
| 4,108,729 | 8/1978 | Mennen . |
| 4,108,972 | 8/1978 | Dreyer . |
| 4,108,976 | 8/1978 | Reese . |
| 4,110,079 | 8/1978 | Schaeffer et al. . |
| 4,116,638 | 9/1978 | Kenoff . |
| 4,123,224 | 10/1978 | Givner et al. . |
| 4,123,509 | 10/1978 | Banik et al. . |
| 4,128,399 | 12/1978 | Liotta et al. . |
| 4,129,417 | 12/1978 | White . |
| 4,130,462 | 12/1978 | Rubenstein et al. . |
| 4,133,639 | 1/1979 | Harte . |
| 4,134,792 | 1/1979 | Boguslaski et al. . |
| 4,144,306 | 3/1979 | Figueras . |
| 4,145,186 | 3/1979 | Andersen . |
| 4,145,406 | 3/1979 | Schick et al. . |
| 4,153,668 | 5/1979 | Hill et al. . |
| 4,157,323 | 6/1979 | Yen et al. . |
| 4,160,008 | 7/1979 | Fenocketti et al. . |
| 4,166,102 | 8/1979 | Johnson . |
| 4,168,146 | 9/1979 | Grubb et al. . |
| 4,169,138 | 9/1979 | Jonsson . |
| 4,175,923 | 11/1979 | Friend . |
| 4,177,253 | 12/1979 | Davies et al. . |
| 4,180,383 | 12/1979 | Johnson . |
| 4,189,304 | 2/1980 | Adams et al. . |
| 4,200,690 | 4/1980 | Root et al. . |
| 4,205,058 | 5/1980 | Wagner et al. . |
| 4,205,952 | 6/1980 | Cais . |
| 4,210,418 | 7/1980 | Brown et al. . |
| 4,219,335 | 8/1980 | Ebersole . |
| 4,223,089 | 9/1980 | Rothe et al. . |
| 4,228,237 | 10/1980 | Hevey et al. . |
| 4,233,029 | 11/1980 | Columbus . |
| 4,233,402 | 11/1980 | Maggio et al. . |
| 4,235,601 | 11/1980 | Deutsch et al. . |
| 4,237,234 | 12/1980 | Meunier . |
| 4,238,565 | 12/1980 | Hornby et al. . |
| 4,243,749 | 1/1981 | Sadeh et al. . |
| 4,244,694 | 1/1981 | Farina et al. . |
| 4,246,339 | 1/1981 | Cole et al. . |
| 4,248,829 | 2/1981 | Kitajima et al. . |
| 4,248,965 | 2/1981 | Mochida et al. . |
| 4,254,082 | 3/1981 | Schick et al. . |
| 4,254,083 | 3/1981 | Columbus . |
| 4,255,384 | 3/1981 | Kitajima et al. . |
| 4,256,693 | 3/1981 | Kondo et al. . |
| 4,258,001 | 3/1981 | Pierce et al. . |
| 4,268,270 | 5/1981 | Gabbay et al. . |
| 4,270,921 | 6/1981 | Graas . |
| 4,271,119 | 6/1981 | Columbus . |
| 4,274,832 | 6/1981 | Wu et al. . |
| 4,275,149 | 6/1981 | Litman et al. . |
| 4,279,617 | 7/1981 | Masson et al. . |
| 4,279,885 | 7/1981 | Reese et al. . |
| 4,280,816 | 7/1981 | Elahi . |
| 4,281,061 | 7/1981 | Zuk et al. . |
| 4,288,228 | 9/1981 | Oberhardt . |
| 4,298,345 | 11/1981 | Sodickson et al. . |
| 4,298,685 | 11/1981 | Parikh et al. . |
| 4,299,916 | 11/1981 | Litman et al. . |
| 4,301,139 | 11/1981 | Feingers et al. . |
| 4,305,720 | 12/1981 | Bernstein . |
| 4,305,721 | 12/1981 | Bernstein . |
| 4,305,924 | 12/1981 | Piasio et al. . |
| 4,313,734 | 2/1982 | Leuvering . |
| 4,315,907 | 2/1982 | Fridlender et al. . |
| 4,318,707 | 3/1982 | Litman et al. . |
| 4,323,536 | 4/1982 | Columbus . |
| 4,332,783 | 6/1982 | Pernice et al. . |
| 4,333,733 | 6/1982 | Sanford et al. . |
| 4,337,065 | 6/1982 | Hiratsuka et al. . |
| 4,338,094 | 7/1982 | Elahi . |
| 4,347,312 | 8/1982 | Brown et al. . |
| 4,357,311 | 11/1982 | Schutt . |
| 4,361,537 | 11/1982 | Deutsch et al. . |
| 4,362,697 | 12/1982 | Tabb et al. . |
| 4,363,874 | 12/1982 | Greenquist . |
| 4,365,970 | 12/1982 | Lawrence et al. . |
| 4,366,241 | 12/1982 | Tom et al. . |
| 4,373,932 | 2/1983 | Gribnau et al. . |
| 4,374,925 | 2/1983 | Litmanm et al. . |
| 4,376,110 | 3/1983 | David et al. . |
| 4,380,580 | 4/1983 | Boguslaski et al. . |
| 4,390,343 | 6/1983 | Walter . |
| 4,391,904 | 7/1983 | Litman et al. . |
| 4,407,943 | 10/1983 | Cole et al. . |
| 4,411,518 | 10/1983 | Meserol et al. . |
| 4,425,438 | 1/1984 | Cole et al. . |
| 4,426,451 | 1/1984 | Columbus . |

| | | | | | | |
|---|---|---|---|---|---|---|
| 4,435,504 | 3/1984 | Zuk et al. . | | 4,789,629 | 12/1988 | Baker et al. . |
| 4,442,204 | 4/1984 | Greenquist et al. . | | 4,790,979 | 12/1988 | Terminiello et al. . |
| 4,444,193 | 4/1984 | Fogt et al. . | | 4,797,260 | 1/1989 | Parker . |
| 4,446,232 | 5/1984 | Liotta . | | 4,803,048 | 2/1989 | Nason . |
| 4,447,526 | 5/1984 | Rupchock et al. . | | 4,803,154 | 2/1989 | Uo et al. . |
| 4,447,529 | 5/1984 | Greenquist et al. . | | 4,803,170 | 2/1989 | Stanton et al. . |
| 4,447,546 | 5/1984 | Hirschfeld . | | 4,806,311 | 2/1989 | Greenquist . |
| 4,450,231 | 5/1984 | Ozkan . | | 4,806,312 | 2/1989 | Greenquist . |
| 4,452,901 | 6/1984 | Gordon et al. . | | 4,810,470 | 3/1989 | Burkhardt et al. . |
| 4,459,358 | 7/1984 | Berke . | | 4,812,293 | 3/1989 | McLaurin et al. . |
| 4,461,829 | 7/1984 | Greenquist . | | 4,814,142 | 3/1989 | Gleisner . |
| 4,464,552 | 8/1984 | Pawlowski . | | 4,816,224 | 3/1989 | Vogel et al. . |
| 4,472,498 | 9/1984 | Masuda et al. . | | 4,818,677 | 4/1989 | Hay-Kaufman et al. . |
| 4,474,878 | 10/1984 | Halbert et al. . | | 4,826,759 | 5/1989 | Guire et al. . |
| 4,477,575 | 10/1984 | Vogel et al. . | | 4,837,145 | 6/1989 | Liotta . |
| 4,486,530 | 12/1984 | David et al. . | | 4,837,168 | 6/1989 | de Jaeger et al. . |
| 4,504,585 | 3/1985 | Reynolds . | | 4,837,373 | 6/1989 | Gunkel et al. . |
| 4,506,009 | 3/1985 | Lenhoff et al. . | | 4,837,395 | 6/1989 | Leeder et al. . |
| 4,514,507 | 4/1985 | Secher . | | 4,843,000 | 6/1989 | Litman et al. . |
| 4,517,288 | 5/1985 | Giegel et al. . | | 4,847,199 | 7/1989 | Snyder et al. . |
| 4,533,629 | 8/1985 | Litman et al. . | | 4,849,338 | 7/1989 | Litman et al. . |
| 4,540,659 | 9/1985 | Litman et al. . | | 4,849,340 | 7/1989 | Oberhardt . |
| 4,550,075 | 10/1985 | Bacquet et al. . | | 4,851,210 | 7/1989 | Hewett . |
| 4,552,839 | 11/1985 | Gould et al. . | | 4,851,356 | 7/1989 | Canfield et al. . |
| 4,562,148 | 12/1985 | Sommer . | | 4,853,335 | 8/1989 | Olsen et al. . |
| 4,582,811 | 4/1986 | Pucci et al. . | | 4,855,240 | 8/1989 | Rosenstein et al. . |
| 4,594,327 | 6/1986 | Zuk . | | 4,857,453 | 8/1989 | Ullman et al. . |
| 4,604,365 | 8/1986 | O'Neill et al. . | | 4,859,603 | 8/1989 | Dole et al. . |
| 4,608,336 | 8/1986 | Benovic et al. . | | 4,859,612 | 8/1989 | Cole et al. . |
| 4,613,567 | 9/1986 | Yasoshima et al. . | | 4,861,711 | 8/1989 | Friesen et al. . |
| 4,615,983 | 10/1986 | Koyama . | | 4,868,106 | 9/1989 | Ito et al. . |
| 4,623,461 | 11/1986 | Hossom et al. . | | 4,868,108 | 9/1989 | Bahar et al. . |
| 4,629,690 | 12/1986 | Weng et al. . | | 4,870,005 | 9/1989 | Akiyoshi et al. . |
| 4,631,174 | 12/1986 | Kondo . | | 4,874,692 | 10/1989 | Eikenberry . |
| 4,632,901 | 12/1986 | Valkirs et al. . | | 4,876,067 | 10/1989 | Deneke et al. . |
| 4,639,419 | 1/1987 | Olson et al. . | | 4,877,586 | 10/1989 | Devaney, Jr. et al. . |
| 4,642,285 | 2/1987 | Halbert et al. . | | 4,879,215 | 11/1989 | Weng et al. . |
| 4,656,129 | 4/1987 | Wagner . | | 4,880,751 | 11/1989 | Georghegan . |
| 4,663,278 | 5/1987 | DiNello . | | 4,883,764 | 11/1989 | Kloepfer . |
| 4,666,866 | 5/1987 | Krauth . | | 4,889,816 | 12/1989 | Davis et al. . |
| 4,668,619 | 5/1987 | Greenquist et al. . | | 4,900,663 | 2/1990 | Wie et al. . |
| 4,678,757 | 7/1987 | Rapkin et al. . | | 4,902,629 | 2/1990 | Meserol et al. . |
| 4,681,782 | 7/1987 | Ozkan . | | 4,904,583 | 2/1990 | Mapes et al. . |
| 4,683,197 | 7/1987 | Gallati . | | 4,912,034 | 3/1990 | Kalra et al. . |
| 4,687,732 | 8/1987 | Ward et al. . | | 4,916,056 | 4/1990 | Brown, III et al. . |
| 4,687,735 | 8/1987 | DiNello et al. . | | 4,916,078 | 4/1990 | Klose et al. . |
| 4,690,907 | 9/1987 | Hibino et al. . | | 4,918,025 | 4/1990 | Grenner et al. . |
| 4,693,834 | 9/1987 | Hossom . | | 4,920,045 | 4/1990 | Okuda et al. . |
| 4,703,017 | 10/1987 | Campbell et al. . | | 4,920,046 | 4/1990 | McFarland et al. . |
| 4,711,955 | 12/1987 | Ward et al. . | | 4,923,680 | 5/1990 | Nelson . |
| 4,717,656 | 1/1988 | Swanljung .................................. 435/7 | | 4,931,385 | 6/1990 | Block et al. . |
| 4,722,906 | 2/1988 | Guire . | | 4,933,092 | 6/1990 | Aunet et al. . |
| 4,727,019 | 2/1988 | Valkirs et al. . | | 4,938,927 | 7/1990 | Kelton et al. . |
| 4,738,823 | 4/1988 | Engelmann . | | 4,939,098 | 7/1990 | Suzuki et al. . |
| 4,740,468 | 4/1988 | Weng et al. . | | 4,943,522 | 7/1990 | Eisinger et al. . |
| 4,742,011 | 5/1988 | Blake et al. . | | 4,952,517 | 8/1990 | Bahar . |
| 4,743,560 | 5/1988 | Campbell et al. . | | 4,952,520 | 8/1990 | Okusa et al. . |
| 4,752,562 | 6/1988 | Sheiman et al. . | | 4,956,275 | 9/1990 | Zuk et al. . |
| 4,753,893 | 6/1988 | Roper . | | 4,956,302 | 9/1990 | Gordon et al. . |
| 4,757,002 | 7/1988 | Joo . | | 4,959,197 | 9/1990 | Parekh et al. . |
| 4,757,024 | 7/1988 | Roper . | | 4,959,305 | 9/1990 | Woodrum . |
| 4,760,142 | 7/1988 | Primes et al. . | | 4,959,307 | 9/1990 | Olson . |
| 4,761,381 | 8/1988 | Blatt et al. . | | 4,960,565 | 10/1990 | Shurben . |
| 4,770,853 | 9/1988 | Bernstein . | | 4,960,691 | 10/1990 | Gordon et al. . |
| 4,774,174 | 9/1988 | Giegel et al. . | | 4,960,692 | 10/1990 | Lentrichia et al. . |
| 4,775,636 | 10/1988 | Moeremans et al. . | | 4,963,325 | 10/1990 | Lennon et al. . |
| 4,776,612 | 10/1988 | Cox . | | 4,963,468 | 10/1990 | Olson . |
| 4,780,280 | 10/1988 | Berger et al. . | | 4,976,926 | 12/1990 | Matkovich . |
| 4,782,016 | 11/1988 | Norton . | | 4,977,078 | 12/1990 | Niimura et al. . |
| 4,786,594 | 11/1988 | Khanna et al. . | | 4,981,786 | 1/1991 | Dafforn et al. . |
| 4,788,136 | 11/1988 | Grenier et al. . | | 4,988,627 | 1/1991 | Smith-Lewis . |
| 4,789,526 | 12/1988 | Matkovich . | | 4,990,442 | 2/1991 | Del Campo . |

| | | |
|---|---|---|
| 4,999,285 | 3/1991 | Stiso . |
| 4,999,287 | 3/1991 | Allen et al. . |
| 5,006,464 | 4/1991 | Chu et al. . |
| 5,006,474 | 4/1991 | Horstman . |
| 5,009,996 | 4/1991 | Shah et al. . |
| 5,009,997 | 4/1991 | Shah et al. . |
| 5,024,323 | 6/1991 | Bolton . |
| 5,028,535 | 7/1991 | Buechler et al. . |
| 5,030,555 | 7/1991 | Clemmons . |
| 5,030,558 | 7/1991 | Litman et al. . |
| 5,039,607 | 8/1991 | Skold et al. . |
| 5,051,237 | 9/1991 | Grenner et al. . |
| 5,059,526 | 10/1991 | Arai et al. . |
| 5,064,541 | 11/1991 | Jeng et al. . |
| 5,071,746 | 12/1991 | Wilk et al. . |
| 5,073,484 | 12/1991 | Swanson et al. . |
| 5,075,078 | 12/1991 | Osikowicz et al. . |
| 5,079,142 | 1/1992 | Coleman et al. . |
| 5,079,172 | 1/1992 | Hari et al. . |
| 5,079,174 | 1/1992 | Buck et al. . |
| 5,085,987 | 2/1992 | Olson . |
| 5,085,988 | 2/1992 | Olson . |
| 5,087,556 | 2/1992 | Ertinghausen . |
| 5,089,391 | 2/1992 | Buechler et al. . |
| 5,094,962 | 3/1992 | Snyder et al. . |
| 5,096,809 | 3/1992 | Chen et al. . |
| 5,096,837 | 3/1992 | Fan et al. . |
| 5,100,620 | 3/1992 | Brenneman . |
| 5,104,793 | 4/1992 | Buck . |
| 5,104,811 | 4/1992 | Berger et al. . |
| 5,104,812 | 4/1992 | Kurn et al. . |
| 5,106,758 | 4/1992 | Adler et al. . |
| 5,110,550 | 5/1992 | Schlipfenbacher et al. . |
| 5,114,673 | 5/1992 | Berger et al. . |
| 5,114,862 | 5/1992 | Brenneman . |
| 5,119,941 | 6/1992 | Lepie . |
| 5,120,643 | 6/1992 | Ching et al. . |
| 5,120,662 | 6/1992 | Chan et al. . |
| 5,132,086 | 7/1992 | Allen et al. . |
| 5,132,208 | 7/1992 | Freitag et al. . |
| 5,135,716 | 8/1992 | Thakore . |
| 5,135,872 | 8/1992 | Pouletty et al. . |
| 5,135,873 | 8/1992 | Patel et al. . |
| 5,137,804 | 8/1992 | Greene et al. . |
| 5,137,808 | 8/1992 | Ullman et al. . |
| 5,141,850 | 8/1992 | Cole et al. . |
| 5,141,875 | 8/1992 | Kelton et al. . |
| 5,143,210 | 9/1992 | Warwick et al. . |
| 5,145,784 | 9/1992 | Cox et al. . |
| 5,156,952 | 10/1992 | Litman et al. . |
| 5,158,869 | 10/1992 | Pouletty et al. . |
| 5,158,895 | 10/1992 | Ashihara et al. . |
| 5,160,486 | 11/1992 | Schlipfenbacher et al. . |
| 5,162,237 | 11/1992 | Messenger et al. . |
| 5,164,294 | 11/1992 | Skold et al. . |
| 5,177,021 | 1/1993 | Kondo . |
| 5,182,191 | 1/1993 | Fan et al. . |
| 5,182,216 | 1/1993 | Clayton et al. . |
| 5,185,127 | 2/1993 | Vonk . |
| 5,188,939 | 2/1993 | Mangold et al. . |
| 5,188,966 | 2/1993 | Eikmeier et al. . |
| 5,202,267 | 4/1993 | Ditlow et al. . |
| 5,202,268 | 4/1993 | Kuhn et al. . |
| 5,206,177 | 4/1993 | DeLaCroix et al. . |
| 5,209,904 | 5/1993 | Forney et al. . |
| 5,211,914 | 5/1993 | Vogel et al. . |
| 5,212,060 | 5/1993 | Maddox . |
| 5,215,886 | 6/1993 | Patel et al. . |
| 5,223,436 | 6/1993 | Freitag et al. . |
| 5,232,835 | 8/1993 | Litman et al. . |
| 5,234,813 | 8/1993 | McGeehan et al. . |
| 5,236,826 | 8/1993 | Marshall . |
| 5,238,652 | 8/1993 | Sun et al. . |
| 5,240,862 | 8/1993 | Koenhen et al. . |
| 5,248,619 | 9/1993 | Skold et al. . |
| 5,252,492 | 10/1993 | Yoshikami . |
| 5,256,372 | 10/1993 | Brooks et al. . |
| 5,258,163 | 11/1993 | Krause et al. . |
| 5,260,193 | 11/1993 | Olson . |
| 5,260,194 | 11/1993 | Olson . |
| 5,260,222 | 11/1993 | Patel et al. . |
| 5,264,180 | 11/1993 | Allen et al. . |
| 5,275,785 | 1/1994 | May et al. . |
| 5,278,079 | 1/1994 | Gubinski et al. . |
| 5,294,369 | 3/1994 | Shigekawa et al. . |
| 5,308,580 | 5/1994 | Clark . |
| 5,310,804 | 5/1994 | Boguslaski et al. . |
| 5,656,503 | 8/1997 | May et al. . |

FOREIGN PATENT DOCUMENTS

| | | |
|---|---|---|
| 0170746 | 2/1986 | European Pat. Off. . |
| 0183442 | 6/1986 | European Pat. Off. . |
| 0191640 | 8/1986 | European Pat. Off. . |
| 0217403 | 4/1987 | European Pat. Off. . |
| 0225054 | 6/1987 | European Pat. Off. . |
| 0227173 | 7/1987 | European Pat. Off. . |
| 0238012 | 9/1987 | European Pat. Off. . |
| 0250137 | 12/1987 | European Pat. Off. . |
| 0259157 | 3/1988 | European Pat. Off. . |
| 0262328 | 4/1988 | European Pat. Off. . |
| 0267724 | 5/1988 | European Pat. Off. . |
| 0269362 | 6/1988 | European Pat. Off. . |
| 0269876 | 6/1988 | European Pat. Off. . |
| 0271204 | 6/1988 | European Pat. Off. . |
| 0277723 A1 | 8/1988 | European Pat. Off. . |
| 0279097 | 8/1988 | European Pat. Off. . |
| 0284232 | 9/1988 | European Pat. Off. . |
| 0290921 | 11/1988 | European Pat. Off. . |
| 0291176 | 11/1988 | European Pat. Off. . |
| 0291194 | 11/1988 | European Pat. Off. . |
| 0296724 | 12/1988 | European Pat. Off. . |
| 0297292 | 1/1989 | European Pat. Off. . |
| 0299359 A2 | 1/1989 | European Pat. Off. . |
| 0299428 | 1/1989 | European Pat. Off. . |
| 0309883 | 4/1989 | European Pat. Off. . |
| 0310406 | 4/1989 | European Pat. Off. . |
| 0317001 | 5/1989 | European Pat. Off. . |
| 0319294 | 6/1989 | European Pat. Off. . |
| 0322340 | 6/1989 | European Pat. Off. . |
| 0339450 | 11/1989 | European Pat. Off. . |
| 0342771 | 11/1989 | European Pat. Off. . |
| 0374684 | 6/1990 | European Pat. Off. . |
| 0383619 | 8/1990 | European Pat. Off. . |
| 0407904 | 1/1991 | European Pat. Off. . |
| 0415679 | 3/1991 | European Pat. Off. . |
| 0443231 | 8/1991 | European Pat. Off. . |
| 2016687 | 9/1979 | United Kingdom . |
| 2204398 | 11/1988 | United Kingdom . |
| WO 84/02193 | 6/1984 | WIPO . |
| WO 86/03839 | 7/1986 | WIPO . |
| WO 86/04683 | 8/1986 | WIPO . |
| WO 87/02778 | 5/1987 | WIPO . |
| WO 88/05540 | 7/1988 | WIPO . |
| WO 89/03992 | 5/1989 | WIPO . |
| WO 89/06801 | 7/1989 | WIPO . |
| WO89/06799 | 7/1989 | WIPO . |
| WO 90/5906 | 5/1990 | WIPO . |
| WO 91/01003 | 1/1991 | WIPO . |
| WO 91/19980 | 12/1991 | WIPO . |
| WO 92/01226 | 1/1992 | WIPO . |
| WO 93/03176 | 2/1993 | WIPO . |

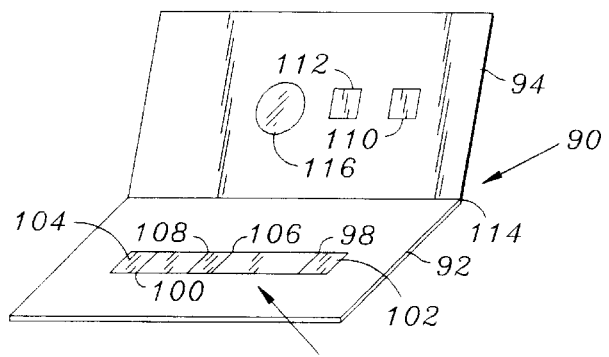
FIG. 4
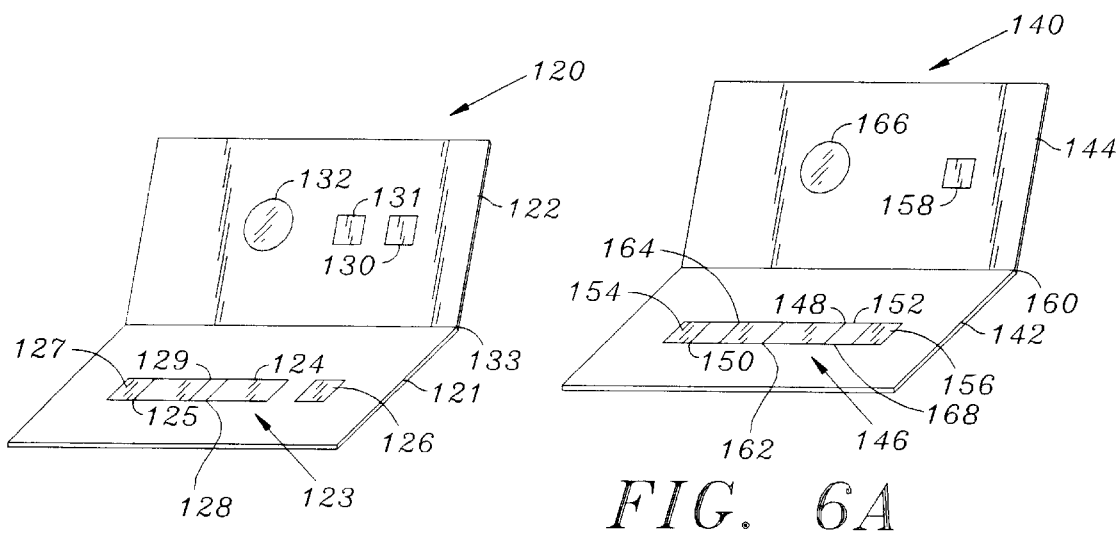
FIG. 5
FIG. 6A
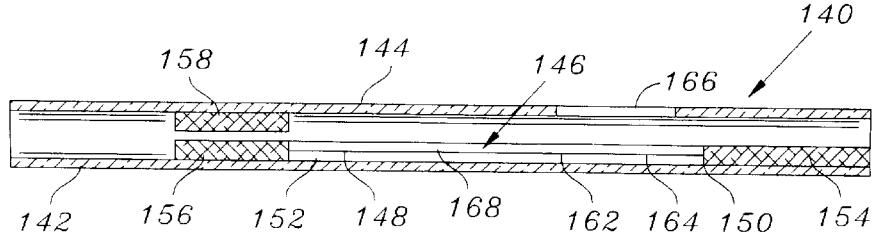
FIG. 6B

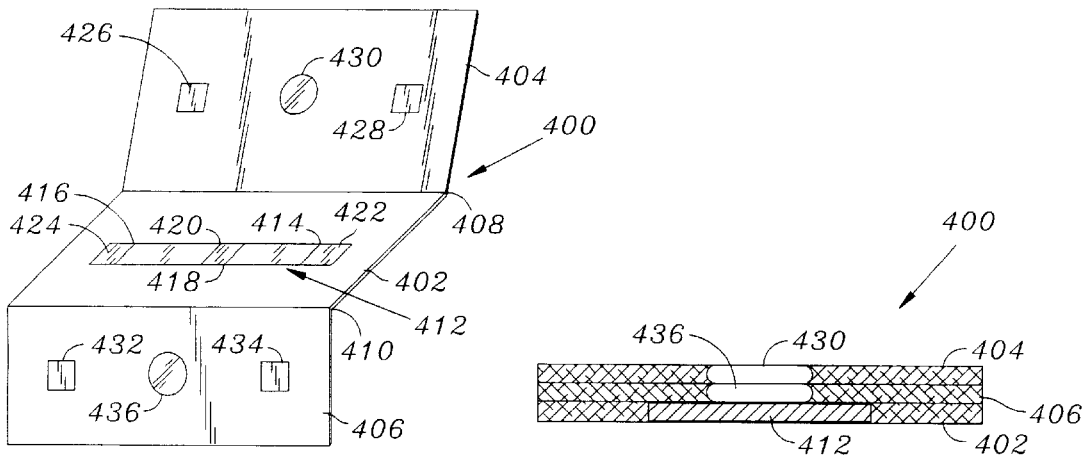
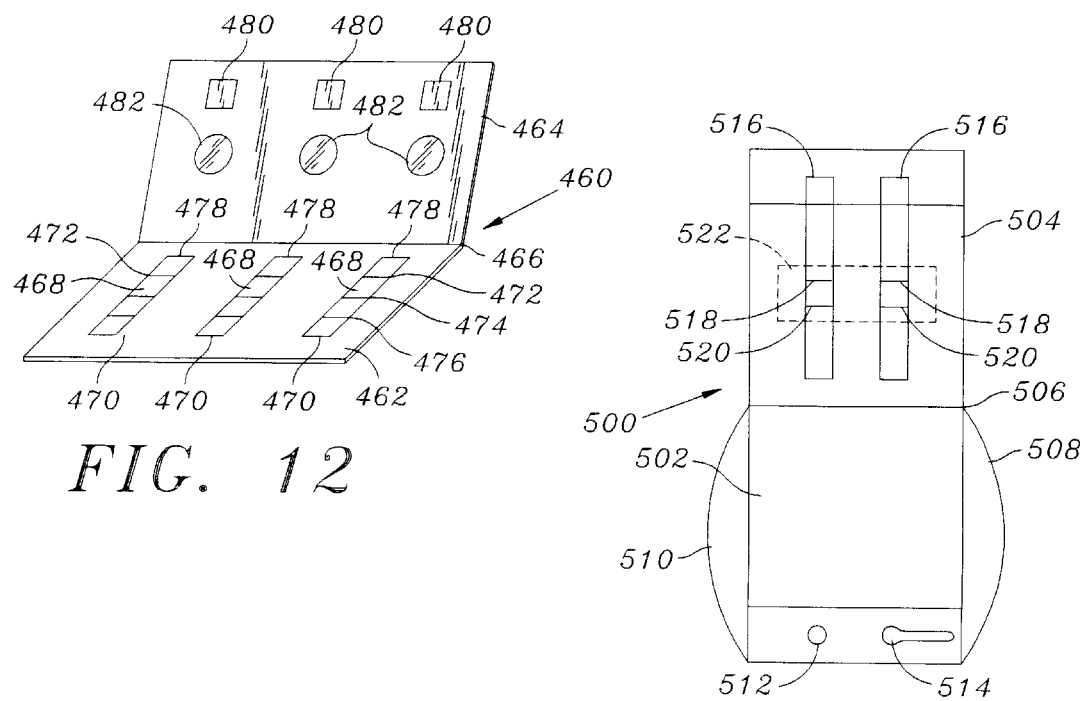

ively used by patients themselves for at-home monitoring of such conditions and disorders.

ASSAY DEVICE

CROSS-REFERENCES

This is a DIVISIONAL application Ser. No. 08/194,793, filed Feb. 10, 1994, which was a file wrapper continuation of application Ser. No. 07/888,831, filed on May 27, 1992, now abandoned which is a continuation-in-part of U.S. application Ser. No. 07/706,639 by Howard M. Chandler, filed May 29, 1991, and also entitled "Assay Device," which is incorporated herein in its entirety by this reference.

BACKGROUND OF THE INVENTION

This invention is directed to test strips for determination of characteristics of samples, unitized housings, and kits incorporating the test strips, and methods of determining the characteristics of samples using the test strips.

Among the many analytical systems used for detection and/or determination of analytes, particularly analytes of biological interest, are chromatographic assay systems. Among the analytes frequently assayed with such systems are:

(1) hormones, such as human chorionic gonadotropin (hCG), frequently assayed as a marker of human pregnancy;

(2) antigens, particularly antigens specific to bacterial, viral, and protozoan pathogens, such as Streptococcus, hepatitis virus, and Giardia;

(3) antibodies, particularly antibodies induced as a result of infection with pathogens, such as antibody to the bacterium *Helicobacter pylori* and to human immunodeficiency virus (HIV);

(4) other proteins, such as hemoglobin, frequently assayed in determinations of fecal occult blood, an early indicator of gastrointestinal disorders such as colon cancer;

(5) enzymes, such as aspartate aminotransferase, lactate dehydrogenase, alkaline phosphatase, and glutamate dehydrogenase, frequently assayed as indicators of physiological function and tissue damage;

(6) drugs, both therapeutic drugs, such as antibiotics, tranquilizers and anticonvulsants, and illegal drugs of abuse, such as cocaine, heroin, and marijuana; and (7) vitamins.

Such chromatographic systems are frequently used by physicians and medical technicians for rapid in-office diagnosis and therapeutic monitoring of a variety of conditions and disorders. They are also increasingly used by patients themselves for at-home monitoring of such conditions and disorders.

Among the most important of such systems are the "thin layer" systems in which a solvent moves across a thin, flat absorbent medium.

Among the most important of tests that can be performed with such thin layer systems are immunoassays, which depend on the specific interaction between an antigen or hapten and a corresponding antibody. The use of immunoassays as a means of testing for the presence and/or amount of clinically important molecules has been known for some time. As early as 1956, J. M. Singer reported the use of an immune-based latex agglutination test for detecting a factor associated with rheumatoid arthritis (Singer et al., *Am. J. Med.* 22:888–892 (1956)).

Among the chromatographic techniques used in conjunction with immunoassays is a procedure known as immunochromatography. In general, this technique uses a disclosing reagent or particle that has been linked to an antibody to the molecule to be assayed, forming a conjugate. This conjugate is then mixed with a specimen and, if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, specific reactivity with another molecule, or another physical or chemical property. The specific reactions that are employed vary with the nature of the molecule being assayed and the sample to be tested.

Immunochromatographic assays fall into two principal categories: "sandwich" and "competitive," according to the nature of the antigen-antibody complex to be detected and the sequence of reactions required to produce that complex. In general, the sandwich immunochromatographic procedures call for mixing the sample that may contain the analyte to be assayed with antibodies to the analyte. These antibodies are mobile and typically are linked to a label or a disclosing reagent, such as dyed latex, a colloidal metal sol, or a radioisotope. This mixture is then applied to a chromatographic medium containing a band or zone. This band or zone contains immobilized antibodies to the analyte of interest. The chromatographic medium often is in the form of a strip resembling a dipstick. When the complex of the molecule to be assayed and the labelled antibody reaches the zone of the immobilized antibodies on the chromatographic medium, binding occurs and the bound labelled antibodies are localized at the zone. This indicates the presence of the molecule to be assayed. This technique can be used to obtain quantitative or semi-quantitative results.

Examples of sandwich immunoassays performed on test strips are described by U.S. Pat. No. 4,168,146 to Grubb et al. and U.S. Pat. No. 4,366,241 to Tom et al. both of which are incorporated herein by this reference.

In addition to immunochromatographic assays, it is also known to use enzyme-based chromatographic assays. These techniques are roughly analogous to immunochromatographic assays, but use an enzymatically catalyzed reaction instead of an antigen-antibody reaction. The enzymatically catalyzed reaction frequently generates a detectable product. Other analogous chromatographic assays are known.

Although useful, currently available chromatographic techniques using test strips have a number of drawbacks. Many samples, such as fecal samples, contain particulate matter that can clog the pores of the chromatographic medium, greatly hindering the immunochromatographic process. Other samples, such as blood, contain cells and colored components that make it difficult to read the test. Even if the sample does not create interference, it is frequently difficult with existing chromatographic test devices to apply the sample to the chromatographic medium so that the sample front moves uniformly through the chromatographic medium to insure that the sample reaches the area where binding is to occur in a uniform, straight-line manner.

Sample preparation and waste generation are responsible for other problems with currently available devices and techniques for immunochromatography. The increased prevalence of diseases spread by infected blood and blood fractions, such as AIDS and hepatitis, has exacerbated these problems. It is rarely possible to apply a sample (such as feces) or a sampling device (such as a throat swab) directly to the chromatographic medium. Several extraction and pretreatment reactions are usually required before the sample can be applied to the chromatographic medium. These reactions are typically carried out by the physician or technician performing the test in several small vessels, such as test tubes, or microfuge tubes, requiring the use of transfer devices, such as pipettes. Each of these devices is then contaminated and must be disposed of using special precautions so that workers or people who may inadvertently come into contact with the waste do not become contaminated.

Still another limitation on chromatographic devices currently available for use by the clinician or technician is their inability to perform two-directional or two-dimensional chromatography. These techniques have long been known to be powerful analytical tools, but their complexity relative to simple unidirectional chromatography has made it difficult to apply them to test strip devices in the physician's office or a clinical laboratory.

Accordingly, there is a need for an improved chromatographic device for the performance of immunochromatographic assays or other analogous assays. Such a device should be capable of receiving a possibly contaminated sample or a sample preparation device directly so as to eliminate the need for extraction vessels and transfer devices. Such a device, preferably in the form of a test strip, should also be capable of performing immunochromatographic assays on colored samples or samples containing particulates without interference and should-be able to deliver the sample to the chromatographic medium uniformly and evenly to improve accuracy and precision of the tests. Additionally, such an improved test strip should be capable of performing two-directional or two-dimensional chromatography when used in clinical laboratories or physicians' offices.

SUMMARY

We have developed an assay device that meets these needs and provides improved assays for analytes of biological interest, while simplifying the performance of the assay and avoiding contamination.

In general, a chromatographic assay device according to the present invention comprises:

(1) a first opposable component including a sample preparation means adapted to receive a sample to be assayed; and (2) a second opposable component including a chromatographic medium.

The first and second opposable components can be brought into opposition so as to cause the sample preparation means to apply the sample to be tested to the chromatographic medium.

The sample preparation means can contain at least one reagent for treatment of the sample before the sample is applied to the chromatographic medium. Preferably, the reagent is an extraction reagent to extract analyte from the sample.

The first and second opposable components can each further include engaging means that secure the first and second opposable components in opposition. The first and second opposable components can be joined by a hinge.

Typically, the chromatographic medium has first and second ends and the device further comprises conducting means in operable contact with the first end of the chromatographic medium.

Preferably, the chromatographic medium further includes a detection zone substantially smaller than the chromatographic medium. More preferably, the detection zone contains a first specific binding partner to the analyte immobilized thereto. If the analyte is an antigen or hapten, the first specific binding partner can be an antibody to the antigen or hapten. If the analyte is an antibody, the first specific binding partner can be a hapten or antigen capable of being bound specifically by the antibody.

Preferably, the chromatographic medium further includes a control zone substantially smaller than the chromatographic medium and separate from the detection zone. Typically, the control zone contains analyte immobilized thereto, but other arrangements are possible, depending on the chemical nature of the analyte.

Preferably, the device further comprises an absorbing means in operable contact with the second end of the chromatographic medium to enhance the flow of the sample through the chromatographic medium.

The sample preparation means can further contain a specific binding partner for the analyte labelled with a detectable label in a form that can be resolubilized by the addition of an aqueous liquid to the sample preparation means.

In the device, at least one of the first and second opposable components can include an aperture therein for viewing of at least a portion of the chromatographic medium.

A test kit can comprise the chromatographic assay device described above and a specific binding partner for the analyte labelled with a detectable label. Preferably, the label is a visually detectable label.

A method for detecting and/or determining an analyte in a sample using this assay device can comprise the steps of:

(1) applying the sample to the sample preparation means of the chromatographic assay device;

(2) applying a detection reagent to the sample preparation means, the detection reagent comprising at least one component capable of binding specifically to analyte present in the sample;

(3) bringing the first and second opposable components into opposition so that the sample preparation means applies the sample and the detection reagent to the chromatographic medium;

(4) allowing the sample and the detection reagent to move through at least a portion of the chromatographic medium so that the detection reagent gives a detectable indication of the presence and/or quantity of the analyte; and (5) observing and/or measuring the detection reagent in at least a portion of the chromatographic medium in order to detect and/or determine the analyte.

If the sample preparation means further contains a specific binding partner for the analyte labelled with a detectable label in a form that can be resolubilized by the addition of an aqueous liquid to the sample preparation means, an assay method can comprise the steps of:

(1) applying the sample as an aqueous liquid to the sample preparation means of the chromatographic assay device, thereby resolubilizing the specific binding partner for the analyte with the detectable label so that the labelled specific binding partner can bind specifically to analyte present in the sample;

(2) bringing the first and second opposable components into opposition so that the sample preparation means applies the sample and the labelled specific binding partner to the chromatographic medium;

(3) allowing the sample and the labelled specific binding partner to move through at least a portion of the chromatographic medium so that the labelled specific binding partner gives a detectable indication of the presence and/or quantity of the analyte; and (4) observing and/or measuring the labelled specific binding partner in at least a portion of the chromatographic medium in order to detect and/or determine the analyte.

Another embodiment of an immunoassay device according to the present invention comprises:

(1) a first opposable component including:
   (a) a chromatographic medium having first and second ends; and
   (b) a first application means at the first end of the chromatographic medium; and (2) a second opposable component including:
   (a) a second application means; and
   (b) an absorbing means separated from the second application means.

In this device, addition of a first liquid to the first application means causes the first liquid to be applied to the first end of the chromatographic medium. Bringing the first and second opposable components into opposition: (i) causes the second application means to come into operable contact with the second end of the chromatographic medium so as to apply a second liquid to the second end of the chromatographic medium; and (ii) causes the absorbing means to come into operable contact with the first application means so as to withdraw fluid from the chromatographic medium via the first application means.

This device is suitable for bi-directional chromatography, combined with direct extraction of an analyte in situ.

This embodiment of the device can be used for an assay method in which a detection reagent is applied as the second liquid to the second application means. The detection reagent comprises at least one component capable of binding specifically to analyte present in the sample. Subsequently, the first and second opposable components are brought into opposition. This causes the second application means to come into operable contact with the second end of the chromatographic medium so as to apply the second liquid to the second end of the chromatographic medium, and causes the absorbing means to come into operable contact with the first application means. This then causes the detection reagent to move through at least a portion of the chromatographic medium at least partially overlapping the portion of the chromatographic medium through which the sample moved, so that the detection reagent gives a detectable indication of the presence and/or quantity of the analyte.

Another embodiment of an assay device according to the present invention comprises:

(1) a first opposable component including:
   (a) a sample preparation means adapted to receive a sample to be assayed; and
   (b) a chromatographic medium that is not in operable contact with the sample preparation means; and (2) a second opposable component including a fluid-conducting connecting member.

In this embodiment, when the first and second opposable components are brought into opposition, the connecting member is brought into operable contact with both the sample preparation means and the chromatographic medium so as to result in the application of the sample to the chromatographic medium.

Still another embodiment of an assay device according to the present invention comprises:

(1) a first opposable component including:
   (a) a chromatographic medium having first and second ends;
   (b) a first application means in operable contact with the first end of the chromatographic medium; and
   (c) a first absorbing means of finite capacity in operable contact with the second end of the chromatographic medium; and (2) a second opposable component including:
   (a) a second application means; and
   (b) a second absorbing means.

In this device, the first and second opposable components can be brought into opposition so that the second application means is placed in operable contact with the first absorbing means of finite capacity and the second absorbing means is placed in operable contact with the first application means. This device is also suitable for bidirectional chromatography, in which the sample flows through the chromatographic medium in one direction and a detecting reagent flows through the chromatographic medium in the reverse direction.

In an assay method using this device, typically the sample is applied to the first application means of the chromatographic assay device so that the sample flows through at least a portion of the chromatographic medium from the first end toward the second end. A detection reagent is then applied to the second application means, and the first and second opposable components are brought into opposition. This applies the detection reagent to the chromatographic medium. The detection reagent then flows through at least a portion of the chromatographic medium from the second end to the first end, so that the detection reagent gives a detectable indication of the presence and/or quantity of the analyte.

Yet another embodiment of an assay device according to the present invention comprises:

(1) A first opposable component including;
   (a) a chromatographic medium having first and second ends;
   (b) a first application means in operable contact with the first end of the chromatographic medium and located in a recess of the first opposable component; and
   (c) a first absorbing means in operative contact with the second end of the chromatographic medium;

(2) a second opposable component including:
   (a) a second absorbing means; and
   (b) a second application means separated from the second absorbing means; and (3) a cover hingedly attached to the first opposable component so that it can be folded over the first and second opposable components when they are opposed.

In this device, addition of a first liquid to the first application means causes the first liquid to be applied to the first end of the chromatographic medium. Bringing the first and second opposable components into opposition: (i) causes the second application means to come into operable contact with the first absorbing means so as to apply a second liquid to the second end of the chromatographic medium; and (ii) causes the second absorbing means to come into operable contact with the first application means and into direct contact with at least a portion of the chromatographic medium so as to withdraw fluid from the chromatographic medium via the first application means. The cover is then folded over the first and second opposable components. This device is particularly useful in avoiding interference caused by large sample volumes.

This device is useful in performance of an assay method as described above. In this assay method, the sample is the first liquid and a detection reagent is the second liquid.

Yet another embodiment of an assay device according to the present invention comprises:

(1) a first opposable component including:
   (a) a chromatographic medium having first and second ends;

(b) a first conducting means in operable contact with the first end of the chromatographic medium; and (c) a second conducting means in operable contact with the second end of the chromatographic medium;

(2) a second opposable component hingedly attached to the first opposable component including:

(a) a first absorbing means; and (b) a first application means separated from the first absorbing means; and (1) a third opposable component hingedly attached to the first opposable component including:

(a) a second absorbing means; and (b) a second application means separated from the second absorbing means.

In this device, bringing the first and second opposable components into opposition causes the first absorbing means to come into operable contact with the second conducting means to withdraw fluid from the chromatographic medium, and causes the first application means to come into operable contact with the first conducting means to apply fluid to the chromatographic medium, so that a first liquid applied to the first application means is drawn through at least a portion of the chromatographic medium. Also, subsequently, bringing the first and third opposable components into opposition causes the second absorbing means to come into operable contact with the first conducting means to withdraw fluid from the chromatographic medium and causes the second application means to come into operable contact with the second conducting means to apply fluid to the chromatographic medium so that a second liquid applied to the second application means is drawn through at least a portion of the chromatographic medium overlapping the portion of the chromatographic medium through which the first liquid is drawn. The first, second, and third opposable components are in such a configuration that, that when the third opposable component is brought into opposition with the first opposable component, the second opposable component can be folded over the first and third opposable components to form a cover.

Typically, in this embodiment, the first application means can contain a first specific binding partner for the analyte in a form that can be resolubilized by the application of an aqueous sample to the application means. This embodiment is particularly useful for indirect labeling, in which the first specific binding partner to the analyte is not itself labeled. Rather, a secondary specific binding partner specific for the first binding partner is labeled. This secondary specific binding partner is applied to the second application means to indirectly label the analyte.

Yet another chromatographic assay device according to the present invention comprises:

(1) a first opposable component including:

(a) a sample preparation means; and (b) a chromatographic medium in operable contact with the sample preparation means; and (2) a second opposable component including an application means containing a specific binding partner for the analyte labelled with a detectable label in a form that can be resolubilized by the addition of an aqueous liquid to the application means.

In this device, bringing the first and second opposable components into opposition brings the application means into contact with the sample preparation means such that the labelled specific binding partner for the analyte is resolubilized.

In this embodiment, the first opposable component can further comprise a conducting means, and operable contact between the sample preparation means and the chromatographic medium is achieved by having the sample preparation means and the chromatographic medium both in operable contact with the conducting means.

Another embodiment of an assay device according to the present invention comprises:

(1) a first opposable component including:

(a) a chromatographic medium having first and second ends;

(b) a conducting means in operable contact with the first end of the chromatographic medium; and (3) an absorbing means in operable contact with the second end of the chromatographic medium; and (2) a second opposable component including:

(a) a first application means; and (b) a second application means; the first and second application means being positioned on the second opposable component such that they are not in operable contact when the first and second opposable components are not in opposition.

In this device, bringing the first and second opposable components into opposition places the conducting means in operable contact with the first application means and also places the conducting means in operable contact with the second application means, thereby placing the first and second application means in operable contact with each other.

Yet another version of a chromatographic assay device according to the present invention incorporating two application means on the second opposable component comprises:

(1) a first opposable component including:

(a) a chromatographic medium having first and second ends;

(b) a conducting means positioned such that it is not in operable contact with the first end of the chromatographic medium with the first opposable component and second opposable component are not in opposition; and (c) an absorbing means in operable contact with the second end of the chromatographic medium; and (2) a second opposable component comprising:

(a) a first application means; and (b) a second application means.

The first and second application means are positioned on the second opposable component such that they are not in operable contact when the first and second opposable components are not in opposition. In this device, bringing the first and second opposable components into opposition places the conducting means in operable contact with the first application means, places the conducting means in operable contact with the second application means, and places the second application means in operable contact with the first end of the chromatographic medium, thereby placing the first and second application means in operable contact with each other to apply the contents of the first and second application means to the chromatographic medium.

Another embodiment of an assay device according to the present invention comprises:

(1) a first opposable component including:

(a) a chromatographic medium having first and second ends;

(b) a conducting means in operable contact with the first end of the chromatographic medium;

(c) an absorbing means in operable contact with the second end of the chromatographic medium; and (d) a detector application pad in direct contact with the conducting means and positioned such that it is in indirect contact with the first end of the chromatographic medium; and (b) a second opposable component including a sample application pad.

In this device, bringing the first and second opposable components into opposition causes the sample application pad to apply the sample to be tested to the detector application pad and thus to the first end of the chromatographic medium though the conducting means.

A variation of this device can provide superior dynamic range for analytes such as hemoglobin in feces. This variation comprises:

(1) a first opposable component including:
   (a) a chromatographic medium having first and second ends;
   (b) an absorbing means in operable contact with the second end of the chromatographic medium; and
   (c) a detector application pad in direct contact with the first end of the chromatographic medium; and (2) a second opposable component including a sample application pad.

In this variation, when the first and second opposable components are brought into opposition, the detector application pad and the sample application pad are in contact except for the region of the detector application pad directly adjacent to the first end of the chromatographic medium. Also, bringing the first and second opposable components into opposition causes the sample application pad to apply the sample to be tested to the detector application pad and thus to the first end of the chromatographic medium.

Other embodiments of assay devices according to the present invention are suitable for performing multiple assays. One such embodiment comprises:

(1) a first opposable component including a plurality of sample preparation means, each adapted to receive a sample of the assay; and (2) a second opposable component including as many chromatographic media as are present sample preparation means on the first opposable component.

In this device, the first and second opposable components can be brought into opposition so as to cause each sample preparation means to apply each sample to be tested to the corresponding chromatographic medium. At least one sample preparation means can comprise a collapsible well adapted for receiving a sample-containing device.

Another multiplex device according to the present invention is adapted to receive a test card containing a plurality of dried specimens, such as stool samples. This device comprises:

(1) a first opposable component adapted to receive the test card;

(2) a second opposable component including a reagent pad that is placed in contact with the specimens when the test card is placed in the first opposable component and the first and second opposable components are brought into opposition; and (3) a third opposable component including a plurality of chromatographic media, one for each sample to be tested.

In this device, adding an aqueous reagent to the reagent pad, placing the first and second opposable components into opposition, and placing the second and third opposable components into opposition applies the sample and the contents of the reagent pad to the chromatographic media. Such a device can be used to detect hemoglobin in a fecal sample.

Yet another chromatographic assay device of the present invention adapted to receive a test card comprises:

(1) a first opposable component including a plurality of laterally separated reagent pads; and (2) a second opposable component adapted to receive a test card containing a plurality of dried specimens, the second opposable component including:
   (a) a chromatographic medium for each sample preparation means on the first opposable component, the chromatographic media being laterally separated, each chromatographic medium having a first and a second end;
   (b) a conducting means in operable contact with the first end of each chromatographic medium and in operable contact with each dried specimen of the test card; and
   (c) an absorbing means in operable contact with the second end of each chromatographic medium.

In this device, the first and second opposable components can be brought into opposition so as to cause each reagent pad to be applied to the corresponding dried specimen. The reagent pads typically contain a resolubilizable labeled specific binding partner for the analyte.

BRIEF DESCRIPTION OF THE DRAWINGS

These and other features, aspects, and advantages of the present invention will become better understood with reference to the following description, appended claims, and accompanying drawings where:

FIG. 4 is a drawing of yet another version of a two-component assay device according to the present invention incorporating two application means on one of the components;

FIG. 5 is a drawing of yet another version of a two-component assay device according to the present invention incorporating a discontinuity between a conducting means and the chromatographic medium that is bridged when the device is closed;

FIG. 6A is a drawing of yet another version of a two-component assay device according to the present invention incorporating a detector application pad in operative contact with the chromatographic medium;

FIG. 6B is a side view of the two-component assay device of FIG. 6A, showing details of the components in opposition;

FIG. 11A is a drawing of a three-component assay device according to the present invention;

FIG. 11B is a side view of the three-component assay device of FIG. 11A, showing details of the components in opposition;

FIG. 12 is a drawing of a multiplex assay device according to the present invention, suitable for the simultaneous assay of one or more samples;

FIG. 13 is a drawing of another version of a multiplex assay device according to the present invention, containing a collapsible well to accommodate a sample;

DESCRIPTION

Definitions

Figure 1A:
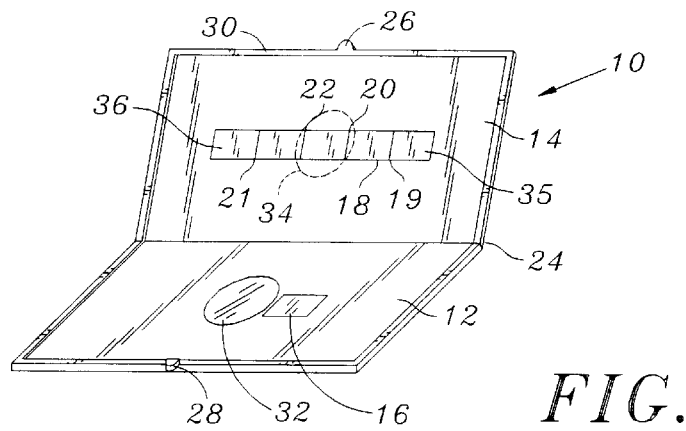
FIG. 1A is a drawing of one version of a two-component chromatographic assay device according to the present invention.

In the context of this disclosure, the following terms are defined as follows unless otherwise indicated:

Specific Binding Partner: A member of a pair of molecules that interact by means of specific non-covalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, inhibitor-enzyme, carbohydrate-lectin, biotin-avidin, and virus-cellular receptor.

Operable Contact: Two solid components are in operable contact when they are in contact, either directly or indirectly, in such a manner that an aqueous liquid can flow from one of the two components to the other substantially uninterruptedly, by capillarity or otherwise. "Direct contact" means that the two elements are in physical contact, such as edge-to-edge or front-to-back. "Indirect contact" means that the two elements are not in physical contact, but are bridged by one or more conducting means.

Finite Capacity: An absorbing means has finite capacity when it becomes saturated by liquid received during the normal performance of an assay in the device in which the absorbing means is located. At that point, the absorbing means can release additional liquid absorbed and become at least partially conductive.

Analyte: The term "analyte" includes both the actual molecule to be assayed and analogues and derivatives thereof when such analogues and derivatives bind another molecule used in the assay in a manner substantially equivalent to that of the analyte itself.

Antibody: The term "antibody" includes both intact antibody molecules of the appropriate specificity and antibody fragments (including Fab, F(ab'), and F(ab')$_2$ fragments) as well as chemically modified intact antibody molecules and antibody fragments, including hybrid antibodies assembled by in vitro reassociation of subunits.

Secondary Specific Binding Partner: An additional specific binding partner that binds to a member of a pair of specific binding partners when the pair of specific binding partners is interacting is designated a secondary specific binding partner. For example, a pair of specific binding partners can comprise Giardia antigen and rabbit anti-Giardia antibody. In that case, the secondary specific binding partner can be goat anti-rabbit IgG antibody. The secondary specific binding partner can be specific for the species, class, or subclass of an antibody specific binding partner to which it binds. Alternatively, when one of the specific binding partners is labelled with biotin, the secondary specific binding partner can comprise a molecule conjugated to avidin.

I. Chromatographic Assay Devices

One aspect of the present invention comprises chromatographic assay devices particularly useful for the assay of analytes in biological samples. These devices are suitable for the direct application of biological samples, without preliminary extraction steps, and are constructed so as to minimize interference with assay results caused by particulates or colored samples.

A. Two-Component Devices

One embodiment of the assay device of the present invention is a two-component chromatographic assay device operating in one dimension with one-directional flow.

1. General Arrangement of Two-Component Device

In general, a two-component chromatographic assay device according to the present invention comprises:

(1) A first opposable component including a sample preparation means adapted to receive a sample to be assayed; and (2) A second opposable component including a chromatographic medium. 8849

In this device, the first and second opposable components can be brought into opposition when the device is closed so as to cause a sample preparation means to apply the sample to be assayed to the chromatographic medium. In use, the first and second opposable components are typically brought into opposition after a detection reagent is applied to the sample preparation means. When the first and second opposable components are brought into opposition, the sample preparation means applies the sample and detection reagent to the chromatographic medium. After the sample and detection reagent is allowed to traverse at least a portion of the chromatographic medium, so that the detection reagent gives a detectable indication of the presence and/or quantity of the analyte; the detection reagent is then observed and/or measured in at least a portion of the chromatographic medium. This results in detection and/or determination of the analyte.

The detection reagent comprises the first specific binding partner for the analyte as described above; it may comprise additional components.

This process can give a qualitative and/or quantitative indication of the analyte, depending upon the density of the second specific binding partner in the detection zone and the size of the detection zone.

Typically, to achieve results, the assay requires from 30 seconds to 10 minutes, more typically, from 1 to 5 minutes, including any period of incubation of the sample on the sample preparation means, as well as the time required for chromatography itself. Typically, the assay is performed at room temperature, although it can be performed at 4° C. or up to 37° C. or higher in some cases, depending upon the nature of the analyte and specific binding partners. In some cases, performing the assay at a lower temperature may be desirable to limit degradation, while in other cases, performing the assay at a higher temperature with suitable analytes and specific binding partners may speed up the assay.

This general arrangement of the chromatographic assay device is shown in FIG. 1A. The chromatographic assay device 10 has a first opposable component 12 and a second opposable component 14. The first opposable component 12 includes a sample preparation means 16. The second opposable component 14 contains a chromatographic medium 18. The chromatographic medium has a first end 19 and a second end 21; the chromatographic medium 18 contains a detection zone 20 and a control zone 22. The first opposable component 12 and the second opposable component 14 are joined by a hinge 24 and have locking means 26 and 28 that are engaged when the first opposable component 12 and the second opposable component 14 are brought into opposition. The sealing ridge or gasket 30 is positioned around the perimeter of the first and second opposable components 12 and 14. The second opposable component 14 has a first window 34; optionally, the first opposable component 12 can have a second window 32 to permit viewing of the chromatographic medium 18 from either side.

Figure 1B:
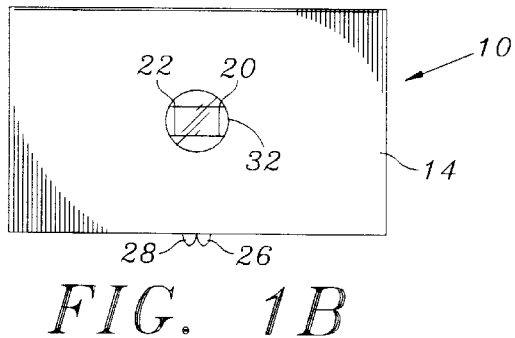
FIG. 1B is a drawing of the two-component chromatographic assay device of FIG. 1A shown with the two components having been brought into opposition.

FIG. 1B shows the device 10 after the opposable components 12 and 14 have been brought into opposition. The chromatographic medium 18, including the detection zone 20 and the control zone 22, is visible through window 34.

The device 10 can, optionally, further comprise conducting means 35 in operable contact with the first end 19 of the chromatographic medium 18, as shown in FIG. 1A. The conducting means 35 can be a material such as cellulose or other material that can conduct an aqueous liquid without substantially absorbing it. The conducting means 35 can be treated with a surfactant so that the conjugate can be applied more evenly to the chromatographic medium.

The device 10 can further comprise an absorbing means 36 in operable contact with the second end 21 of the chromatographic medium 18 to aid in drawing fluid through the chromatographic medium 18 from the first end 19 toward the second end 21, as shown in FIG. 1A.

The sample preparation means can be made of any suitable material, such as, but not limited to, cellulose, paper, nylon, rayon, glass fiber, fleeces, or non-woven synthetic fabrics. The porosity of the sample preparation means can be chosen to filter out cellular or particulate matter in samples such as whole blood or fecal samples. The sample preparation means can contain at least one reagent for treatment of the sample before the sample is applied to the chromatographic medium.

The reagents that can be present in the sample preparation means vary with the sample to be applied to the sample preparation means and with the analyte to be assayed. They can include, but are not limited to, acids or alkalis to adjust the pH, buffers to stabilize the pH, chelating agents such as EDTA or EGTA to chelate metals, hydrolytic enzymes to lyse the cell membrane of animal cells or the cell wall of bacteria to liberate analytes, substrates or co-enzymes for enzymes, and the like. One particularly useful extraction reagent is a mixture of sodium nitrite and acetic acid to generate nitrous acid. The sodium nitrite can be present in dried form on the sample preparation means, and the acetic acid can be added to the sample preparation means after the addition of the sample.

The sample, or optionally, a sampling device such as a throat swab or a microporous filter, can be placed by the operator on the sample preparation means; if needed, other reagents can be added.

The bodies of the first and second opposable components are preferably made of plastic that is impervious to moisture. A suitable plastic is a polycarbonate plastic such as Lexan™. However, other materials, such as paperboard or solid bleached sulfite (SBS), can be used.

Typically, the chromatographic medium, absorbing means, conducting means, application means, and other liquid-receiving components are secured to the bodies of the first and second opposable components by adhesive. Suitable adhesives are well known in the art.

Typically, when two components are in direct contact, they are overlapped with an overlap of about 0.5 to about 3 mm. However, the components can be placed with abutting edges.

The first and second opposable components preferably further comprise engaging means that secure the first and second opposable components in opposition. The engaging means can further comprise locking means.

At least one of the first and second opposable components preferably contains a window or aperture so that the relevant portion of the chromatographic medium can be viewed. Preferably, the window or aperture is located in the second opposable component. Alternatively, both the first and second opposable components can contain a window or aperture to allow viewing of the chromatographic medium from both sides.

A sealing wedge or gasket can be provided around a perimeter of the opposable components to guard against leakage of samples or reagents.

The analyte is detected either by means of a labelled specific binding partner to the analyte or by the use of a labelled secondary specific binding partner for a specific binding partner to the analyte. In most cases, the use of a labelled specific binding partner to the analyte is preferred. The label of the labelled specific binding partner is preferably a visually detectable label, such as a colloidal metal label. Preferably, the colloidal metal label is gold, silver, bronze, iron, or tin; most preferably, it is gold. The preparation of gold-labelled antibodies is described in J. DeMey, "The Preparation and Use of Gold Probes," in *Immunocytochemistry: Modern Methods and Applications* (J. M. Polak & S. VanNoorden, eds. Wright, Bristol, England, 1986), Ch. 8, pp. 115–145, incorporated herein by this reference. Antibodies labelled with colloidal gold are commercially available, such as from Sigma Chemical Company, St. Louis, Mo.

Alternatively, other colloidal labels, such as a colloidal sulfur label, can also be used.

Although Applicant does not necessarily intend to be bound by this theory, when an aqueous liquid containing a sample is applied to a resolubilizible specific binding partner labeled with a colloidal metal label, such as colloidal gold, the kinetics of the reaction between the analyte and the labeled specific binding partner are extremely rapid. These rapid kinetics result in the substantially complete labeling of analyte before the combination of the analyte and the labeled specific binding partner is applied to the chromatographic medium. Thus, in a one-directional chromatographic procedure performed with an assay device according to the present invention, what is chromatographed is predominantly the binary complex of the analyte and the corresponding labeled specific binding partner. This allows separation of this complex from contaminants not binding the specific binding partner and improves accuracy of the assay.

In this embodiment, the labelled specific binding partner preferably is present on the sample preparation means in a form that can be resolubilized by the addition of an aqueous liquid to the sample preparation means. Typically, the aqueous liquid is the sample itself. In some cases, particularly where small sample volumes are used, it may be desirable to add additional buffer or other aqueous liquid to the sample preparation means.

In other embodiments discussed below, the labelled specific binding partner can be present on an element of the chromatographic assay device that is separate from the sample preparation means but comes into contact with it during the performance of the assay. In these embodiments, the labelled specific binding partner is preferably present in a resolubilizable form on this element, and is resolubilized when the sample comes into contact with the element. In some cases, the labelled specific binding partner can be resolubilized by the addition of a separate aqueous liquid, distinct from the sample, to the element.

In a less preferred alternative, the visually detectable label can be a colored latex label. It is also possible to use other labels, such as radioactive labels.

The chromatographic medium on the second opposable component is a flat strip. It is typically rectangular, having first and second ends. Throughout this Description, the term "first end" refers to the end of the chromatographic medium at which the sample is applied, and the term "second end" refers to the opposite end. The original direction of flow of the sample is from the first end toward the second end of the chromatographic medium. The chromatographic medium is composed of a material suitable as a medium for thin-layer chromatography of analytes and analyte-antibody conjugates, such as nitrocellulose, nylon, rayon, cellulose, paper, or silica. The chromatographic medium can be pre-treated or modified as needed. Typically, the chromatographic medium is translucent, so that colored zones appearing on it as a result of the assay can be viewed from either side.

In some applications, it is preferable to place a second flexible transparent support on the top of the chromatographic medium to regulate the flow of the sample through the membrane and prevent migration over the top of the membrane. Suitable flexible transparent supports include polyethylene, vinyl, Mylar®, and cellophane.

When the chromatographic assay device is to be used for an assay such as a sandwich immunoassay, the chromatographic medium can further comprise a detection zone substantially smaller than the chromatographic medium. This detection zone can contain a second specific binding partner to the analyte immobilized thereto against diffusion. The second specific binding partner can be bound to the analyte by either covalent or non-covalent means. If the analyte to be assayed is an antigen or hapten, the second specific binding partner can be an antibody to the antigen or the hapten. Alternatively, the analyte can be an antibody and the second specific binding partner can be a hapten or an antigen capable of being bound specifically by the antibody.

The chromatographic medium can further comprise a control zone substantially smaller than the chromatographic medium, and separate from the detection zone. The control zone can comprise analyte immobilized thereto non-diffusibly in order to bind labelled antibody that is not bound at the detection zone by the formation of a ternary "sandwich" complex. Any such antibody is bound by the immobilized analyte and forms a detectable zone or band. This provides a check on the operation of the assay and the correct binding of the reagents, as described below. The methods used to bind the second specific binding partner in the detection zone and the analyte in the control zone are well known in the art and need not be described further.

Alternatively, for some analytes, such as carbohydrates, it may be difficult or impossible to fix the analyte stably to the chromatographic medium. In such cases, the control zone can comprise an immobilized zone of antibody specific for the labelled anti-analyte antibody. For example, if the analyte is the Streptococcus A-specific carbohydrate, and the labelled antibody is rabbit IgG specific for Streptococcus A antigen, the control zone can comprise goat antibody to rabbit IgG. In such cases, to prevent complete capture of the labelled anti-analyte antibody in the detection zone at high analyte concentrations and consequent disappearance of the labelled anti-analyte antibody from the control zone, it can be desirable to add labelled antibody not specific for the analyte to the labelled anti-analyte antibody. Such antibody can constitute immunologically indifferent immunoglobulin or an antibody to an analyte not found in the test sample.

Several variations of this device are possible. In one variation, as discussed above, the sample preparation means can further contain a specific binding partner for the analyte labelled with a detectable label in a form that can be resolubilized by the addition of an aqueous liquid to the sample preparation means. The aqueous liquid can be the sample itself. The labelled specific binding partner can be freeze-dried or reversibly precipitated so that it is resolubilized and mobilized by the addition of the sample to the sample preparation means. In this variation, it is not necessary to add the detection reagent to the sample preparation means, as the detection reagent is automatically generated by the addition of the sample to the sample preparation means.

In another variation, the second opposable component can further comprise an absorbing means of finite capacity in operable contact with the first end of the chromatographic medium. The absorbing means is located so that it comes into contact with the sample preparation means when the first and second opposable components are placed into opposition. Thus, the sample is applied to the absorbing means when the first and second opposable components are brought into opposition. This may be useful in controlling the flow of sample into the chromatographic medium so that the chromatographic medium is not overloaded.

In this version, the absorbing means can contain a labelled specific binding partner for the analyte in a form that can be resolubilized, as described above. In this arrangement, the labelled specific binding partner is resolubilized when the first and second opposable components are brought into opposition, applying the sample to the absorbing means. The combination of the sample and the resolubilized labelled specific binding partner than enters the chromatographic medium at its first end.

In yet another alternative version of this embodiment, the first opposable component comprises:

(1) A sample preparation means; and (2) A chromatographic medium that is not in communication with the sample preparation means.

The second opposable component comprises a conductive connecting member. The first and second opposable components can be brought into opposition so as to cause the connecting means to establish a communication between the sample preparation means and the chromatographic medium so as to result in the application of the sample to the chromatographic medium.

Figure 2:
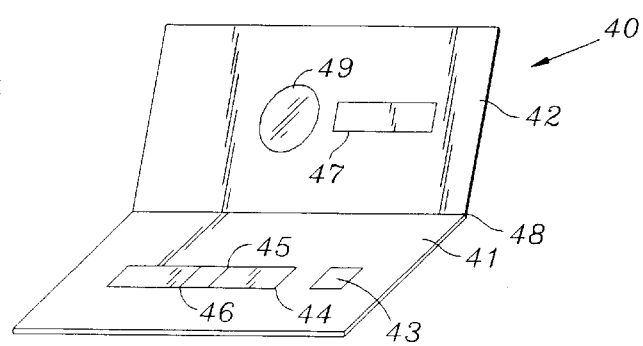
FIG. 2 is a drawing of a version of a two-component chromatographic assay device according to the present invention in which the first opposable component includes a sample preparation means and a chromatographic medium that is not in communication with the sample preparation means, and the second opposable component includes a conductive-connecting member.

This embodiment is depicted in FIG. 2. The chromatographic assay device 40 comprises a first opposable component 41 and a second opposable component 42. The first opposable component includes a sample preparation means 43 and a chromatographic medium 44. The chromatographic medium 44 has a detection zone 45 and a control zone 46. The second opposable component 42 includes a conductive connecting member 47. The first and second opposable components 41 and 42 are connected by a hinge 48. The second opposable component 42 has an window 49 to permit viewing of the chromatographic medium 44.

In variations of the device of FIG. 2, the conductive connecting member 47 can contain a specific binding partner for the analyte labelled with a detectable label in a form that can be resolubilized by the addition of an aqueous liquid. In this variation, the sample is added to the sample preparation means 43. Alternatively, the sample preparation means 43 can be used for addition of labeled specific binding partner for the analyte in liquid form, with the sample itself being added to the conductive connecting member 47. In yet another alternative, the sample preparation means 43 can contain resolubilizable specific binding partner for the analyte, with the sample again being added to the conductive connecting member 47.

2. Particular Embodiments of Two-Component Device a. Device With Sample Preparation Means on First Opposable Component Another embodiment of a chromatographic assay device according to the present invention is a device that incorporates a sample preparation means on the first opposable component, i.e., the component on which the chromatographic medium is located. Typically, in this embodiment, the second opposable component comprises an application means incorporating a labelled specific binding partner for the analyte in a form that can be resolubilized.

In this embodiment, bringing the first and second opposable components into opposition brings the application means into contact with the sample preparation means such that the labelled specific binding partner for the analyte is resolubilized.

Preferably, the first opposable component further comprises a conducting means, and operable contact between the sample preparation means and the chromatographic medium is achieved by having the sample preparation means and the chromatographic medium both in operable contact with the conducting means.

Preferably, the first opposable component further comprises an absorbing means in operable contact with the second end of the chromatography medium.

The chromatographic medium is preferably constructed as described above, with detection and control zones.

Figure 3:
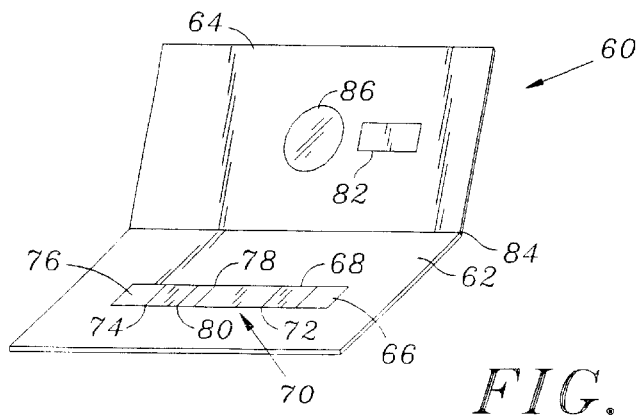
FIG. 3 is a drawing of another version of a two-component assay device according to the present invention with a sample preparation means incorporated into the first opposable component.

This embodiment of the assay device is shown in FIG. 3. The chromatographic assay device 60 has a first opposable component 62 and a second opposable component 64. The first opposable component 62 includes a sample preparation means 66, a conducting means 68 in operable contact with the sample preparation means 66, a chromatographic medium 70 having a first end 72 and a second end 74, and an absorbing means 76 in operable contact with the second end 74 of the chromatographic medium. The chromatographic medium 70 contains a detection zone 78 and a control zone 80. The second opposable component 64 contains an application means 82, preferably incorporating a labeled specific binding partner in a form that can be resolubilized. The first opposable component 62 and the second opposable component 64 are joined by a hinge 84. The second opposable component 62 contains a window 86 to allow viewing of the chromatographic medium 70.

In use, the sample is applied to the sample preparation means, where extraction or other treatment of the sample can occur. The sample then enters the chromatographic medium first end by flowing through the conducting means, as described above. The first and second opposable components are then brought into opposition, which applies the application means to the sample preparation means and accomplishes resolubilization of the labelled specific binding partner. The resolubilized labelled specific binding partner then enters the chromatography medium for the formation of the labelled ternary complex, which is detected after chromatography as described above.

b. Device Comprising Two Separate Application Means on Same Element

Yet another embodiment of a chromatographic assay device according to the present invention comprises two separate application means on the same element. These two application means are not in operable contact until they are bridged by a conducting means on the opposing element when the elements are brought into opposition.

This embodiment of the chromatographic assay device is shown in FIG. 4. The chromatographic assay device 90 has a first opposable component 92 and a second opposable component 94. The first opposable component 92 comprises a chromatographic medium 96 having a first end 98 and a second end 100, a conducting means 102 in operable contact with the first end 98, and an absorbing means 104 in operable contact with the second end 100 of the chromatographic medium 96. The chromatographic medium 96 contains a detection zone 106 and a control zone 108. The second opposable component 94 contains a first application means (sample application pad) 110 and a second application means (detector application pad) 112. The first application means 110 and the second application means 112 are not in operable contact until the first opposable component 92 and the second opposable component 94 are brought into opposition. When the first opposable component 92 and the second opposable component 94 are brought into opposition, the first application means 110 and the second application means 112 are bridged by the conducting means 102 so that the contents of the first application means 110 and the second application means 112 are applied to the chromatographic medium 96. The first opposable component 92 and the second opposable component 94 are joined by a hinge 114. The second opposable component 94 contains a window 116 to allow viewing of the chromatographic medium 96.

The first and second application means are positioned on the second opposable component such that they are not in operable contact when the first and second opposable components are not in opposition. Bringing the first and second opposable components into opposition places the conducting means in operable contact with the first application means and also with the second application means, thereby placing the first and second application means in operable contact with each other. Thus, bringing the first and second opposable components into opposition allows the contents of the first and second application means to react and applies the contents of both the first and second application means to the chromatographic medium. Chromatography and detection of the analyte then occur as described above.

The first application means can comprise a sample application pad and the second application means can comprise a detector application pad, to which detecting reagent can be applied. When the first and second opposable components are brought into opposition, the contents of the sample application pad and the detector application pad are applied to the chromatographic medium via the conducting means.

Preferably, the second application means (detector application pad) contains a specific binding partner for the analyte labelled with a detectable label in a form that can be resolubilized by the addition of an aqueous liquid to the second application means. The aqueous liquid is typically the sample itself, which resolubilizes the labelled specific binding partner when the first and second opposable components are brought into opposition. In some assays, it may be desirable to add a separate reconstituting aqueous liquid to the detector application pad. Alternatively, the labelled specific binding partner can be applied in liquid form to the second application means.

A further variation of this device incorporates a gap or discontinuity between the conducting means and the chromatographic medium so that the path of fluid flow is from the first application means through the conducting means, then through the second application means, and finally through the chromatographic medium.

This variation of the device is shown in FIG. 5. The chromatographic assay device 120 has a first opposable component 121 and a second opposable component 122. The first opposable component 121 comprises a chromatographic medium 123 having a first end 124 and a second end 125, a conducting means 126 not in operable contact with the first end 124 of the chromatographic medium 123 when the device 120 is in open position, and an absorbing means 127 in operable contact with the second end 125 of the chromatographic medium 123. The chromatographic medium 123 contains a detection zone 128 and a control zone 129. The second opposable component 122 contains a first application means (sample application pad) 130 and a second application means (detector application pad) 131. The first application means 130 and the second application means 131 are not in operable contact until the first opposable component 121 and the second opposable component 122 are brought into opposition. When the first opposable component 121 and the second opposable component 122 are brought into opposition, by closing the hinge 133, the first application means 130 and the second application means 131 are bridged by the conducting means 126. Thus, the path of fluid flow is from the first application means 130 through the conducting means 126, then through the second application means 131, and then into the chromatographic medium 123. The second opposable component 122 contains a window 132 to allow viewing of the chromatographic medium 123.

c. Device With Pad for Labelled Specific Binding Partner on Same Opposable Component as Chromatographic Medium Yet another embodiment of a chromatographic assay device according to the present invention is a two-component device incorporating a pad for a labelled specific binding partner on the same opposable component as the chromatographic medium. In this device, the sample application means is located on the other opposable component.

This embodiment of a chromatographic assay device according to the present invention is depicted in FIG. 6A. The chromatographic assay device 140 has a first opposable component 142 and a second opposable component 144. The first opposable component 142 has a chromatographic medium 146 having a first end 148 and a second end 150. The chromatographic medium has a detection zone 162 and a control zone 164. The first opposable component 142 also has a conducting means 152 in operable contact with the first end 148 of the chromatographic medium 146, and an absorbing means 154 in operable contact with the second end 150 of the chromatographic medium 146. The first opposable component 142 also has a detector application pad 156 in direct contact with the conducting means 152 and positioned such that it is in indirect contact with the first end 148 of the chromatographic medium 146. The second opposable component 144 has a sample application pad 158. The first opposable component 142 and the second opposable component 144 are joined by a hinge 160. When the first opposable component 142 and the second opposable component 144 are brought into opposition, the sample application pad 158 is brought into contact with the detector application pad 156. The second opposable component 144 contains a window 166 to allow viewing of the chromatographic medium 146.

A side view of the device 140 is depicted in FIG. 6B. The section shown in FIG. 6B is taken from the view of FIG. 6A between the chromatographic medium 146 and the hinge 160 looking toward the edge opposite the hinge 160. FIG. 6B shows the first opposable component 142 and second opposable component 144 in opposition. The sample application pad 158 is shown in contact with the detector application pad 156. The detector application pad 156 is in contact with the conducting means 152, which is in turn in contact with the first end 148 of the chromatographic medium 146. The detection zone 162 and control zone 164 of the chromatographic medium 146 are shown. The second end 150 of the chromatographic medium 146, nearer the control zone 164, is in contact with the absorbing means 154.

Bringing the first and second opposable components into opposition causes the sample application pad to apply the sample to be tested to the detector application pad and thus to the first end of the chromatographic medium though the conducting means.

Preferably, the detector application pad contains a first specific binding partner to the analyte in a form that can be resolubilized by addition of an aqueous liquid to the detector application pad, and the first specific binding partner is labelled with a detectable label. Preferably, the chromatographic medium further comprises a detection zone substantially smaller in area than the chromatographic medium, as described above. In this arrangement, a ternary complex comprising the first (labelled) specific binding partner, the analyte, and the second specific binding partner forms at the detection zone if analyte is present in the sample. This ternary complex is what is detected or determined.

Preferably, the contents of the sample application pad after a sample is applied thereto comprises an aqueous liquid, and the aqueous liquid applied to the detector application pad comprises the contents of the sample application pad. In this arrangement, there is no additional liquid needed to resolubilize the labelled specific binding partner.

In use, a sample is applied to the sample application pad, and the first and second opposable components are brought into opposition. This applies the sample to the detector application pad, resolubilizing the labelled specific binding partner. The sample and the labelled specific binding partner then flow through the conducting means and into the chromatographic medium for detection and/or determination as described above.

A variation of this device omits the conducting means between the detector application pad and the chromatographic medium, so that the detector application pad is in direct contact with the first end of the chromatographic medium. In this variation, when the first and second opposable components are brought into opposition, the detector application pad and the sample application pad are in contact except for the region of the detector application pad directly adjacent to the first end of the chromatographic medium. There is a slight gap or offset at that region of the detector application pad, so that sample cannot flow directly from the sample application pad to the detector application pad. This gap or offset is typically from about 0.5 mm to about 2 mm, more typically from about 0.5 mm to about 1 mm.

This variation is particularly suitable for the detection of fecal occult blood by use of a labelled anti-hemoglobin antibody, and can detect concentrations of hemoglobin corresponding to as much as 17 ml of blood per 100 g feces (13 mg hemoglobin per gram of feces), without the occurrence of false negatives due to a high dose "hook" effect.

Figure 7A:
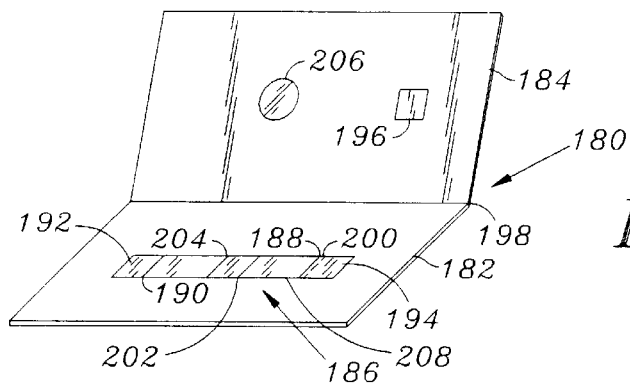
FIG. 7A is a drawing of yet another version of a two-component assay device according to the present invention, generally similar to the version of FIG. 6, but with the detector application pad in direct contact with the chromatographic medium.

This variation is depicted in FIG. 7A. The chromatographic assay device 180 has a first opposable component 182 and a second opposable component 184. The first opposable component 182 has a chromatographic medium 186 having a first end 188 and a second end 190. The chromatographic medium has a detection zone 202 and a control zone 204. The first opposable component 182 also has an absorbing means 192 in operable contact with the second end 190 of the chromatographic medium 186. The first opposable component 182 also has a detector application pad 194 in direct contact with the first end 188 of the chromatographic medium 186. The second opposable component 184 has a sample application pad 196. The first opposable component 182 and the second opposable component 184 are joined by a hinge 198. When the first opposable component 182 and the second opposable component 184 are brought into opposition, the sample application pad 196 is brought into contact with the detector application pad 194, except for a narrow gap or offset 200 at the end of the detector application pad 194 in contact with the first end 188 of the chromatographic medium 186. The second opposable component 184 has a window 206 to allow viewing of the chromatographic medium 186.

Figure 7B:
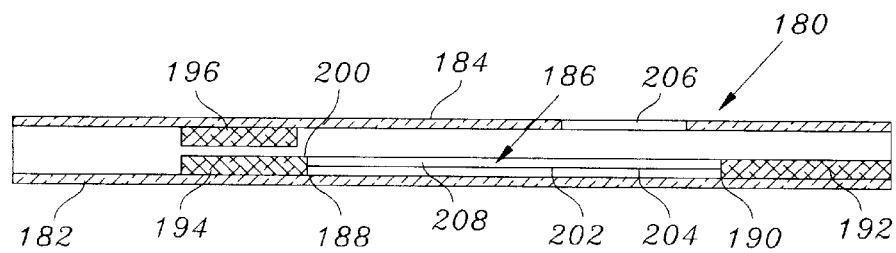
FIG. 7B is a side view of the two-component assay device of FIG. 7A, showing details of the components in opposition.

A side view of the device 180 of FIG. 7A is depicted in FIG. 7B. The section shown in FIG. 7B is taken from the view of FIG. 7A between the chromatographic medium 186 and the hinge 198 looking toward the edge opposite the hinge 190. FIG. 7B shows the first opposable component 182 and second opposable component 184 in opposition, with the hinge 198 in closed position. The sample application pad 196 is shown in contact with the detector application pad 194, except for a small gap 200 at the end of the detector application pad 194 nearest the chromatographic medium 186. This gap 200 prevents sample applied to the sample application pad 196 from flowing directly into the chromatographic medium 186. The detector application pad 194 is in direct contact with the first end 188 of the chromatographic medium 186. The detection zone 202 and control zone 204 of the chromatographic medium 186 are shown. The second end 190 of the chromatographic medium 186, nearer the control zone 204, is in contact with the absorbing means 192.

d. Bi-Directional Device Containing Second Application Means and Absorbing Means on Second Opposable Component Another embodiment of a chromatographic assay device according to the present invention comprises a device capable of carrying out bidirectional chromatography.

Figure 8B:
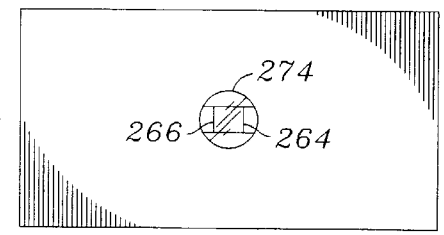
FIG. 8B is a drawing of the two-component chromatographic assay device of FIG. 8A shown with the two components having been brought into opposition.
Figure 8A:
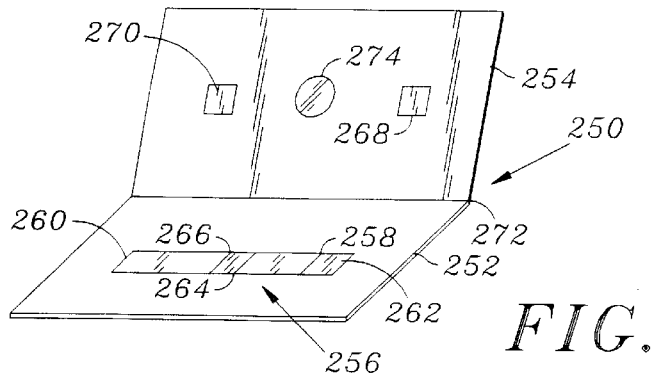
FIG. 8A is a drawing of a version of a two-component assay device according to the present invention suitable for carrying out bi-directional chromatography.

This embodiment of the chromatographic assay device is shown in FIG. 8A. The assay device 250 has a first opposable component 252 and a second opposable component 254. The first opposable component 252 has a chromatographic medium 256 having a first end 258 and a second end 260. The first opposable component 252 also has a first application means 262 in operable contact with the first end 258 of the chromatographic medium 256. The chromatographic medium 256 also further comprises a detection zone 264 and, optionally, a control zone 266 located between the detection zone 264 and the first end 258 of the chromatographic medium 256. The second opposable component 254 includes an absorbing means 268, which can be an absorbent pad, and a second application means 270. The first 252 and second 254 opposable components are joined by a hinge 272. The second opposable component 254 includes a window 274 to permit viewing of the chromatographic medium 256.

When the hinge 272 is closed, the device 250 appears as shown in FIG. 8B. The chromatographic medium 256, including the detection zone 264, and if present, the control zone 266, is visible through window 274.

In this embodiment of the device, addition of a first liquid to the first application means causes the first liquid to be applied to the first end of the chromatographic medium. Bringing the first and second opposable components into opposition then causes the second application means to come into operable contact with the second end of the chromatographic medium so as to apply a second liquid to the second end of the chromatographic medium, and causes the absorbing means to come into operable contact with the first application means so as to withdraw fluid from the chromatographic medium through the first application means. In the operation of this device, the sample is applied to the first application means and a solution of a labelled specific binding partner is applied to the second application means. The sample then moves through the chromatographic medium from the first end to the second end so that any analyte present in the sample is bound to the immobilized antibody at the detection zone. When the first and second opposable components are brought into opposition, the labelled specific binding partner is applied to the chromatographic medium and moves to the chromatographic medium from the second end to the first end. The labelled specific binding partner then binds to any analyte bound to the immobilized antibody at the detection zone, generating a detectable ternary complex.

The device can also comprise a control zone containing the immobilized analyte. In this embodiment, the arrangement of the components, except for the addition of the second application means and the absorbing means, is substantially similar to that of the basic device described above.

e. Bi-Directional Device Containing Two Absorbing Means and Conducting means

Another embodiment of a chromatographic assay device according to the present invention is a device suitable for bi-directional chromatography that contains an absorbing means to reverse the flow and a reagent pad in operable contact with the chromatographic medium.

Figure 9A:
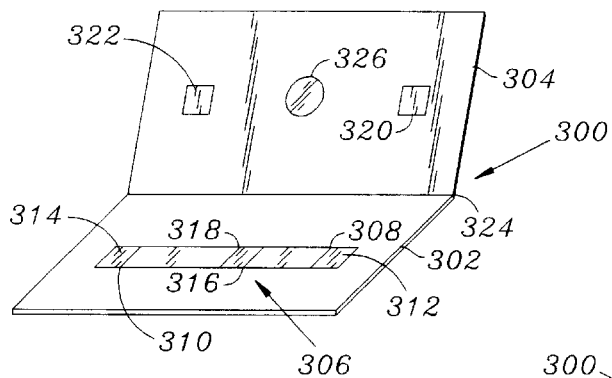
FIG. 9A is a drawing of another version of a two-component assay device suitable for carrying out bi-directional chromatography with two absorbing means and a conducting means.

This embodiment of the chromatographic assay device is shown in FIG. 9A. The assay device 300 has a first opposable component 302 and second opposable component 304. The first opposable component 302 has a chromatographic medium 306 having a first end 308 and a second end 310. Adjacent to and in operable contact with the first end 308 of the chromatographic medium 306 is a first application means 312. Adjacent to and in operable contact with the second end 310 of the chromatographic medium 306 is a conducting means 314. The chromatographic medium 306 contains a detection zone 316, and optionally, a control zone 318. The second opposable component 304 comprises an absorbing means 320 and a second application means 322. The first and second opposable components 302 and 304 are joined by a hinge 324. The second opposable component 304 contains a window 326 to permit viewing of the chromatographic medium 306.

When the first and second opposable components 302 and 304 are brought into opposition, the absorbing means 320 is brought into operable contact with the first application means 312, and the second application means 322 is brought into operable contact with the conducting means 314, thereby reversing the flow. The portion of the chromatographic medium 306, including the detection zone 316 and, if present, the control zone 318, can be viewed through the window 326 in the second opposable component 304 when the first 302 and second 304 opposable components are placed into opposition.

Figure 9B:
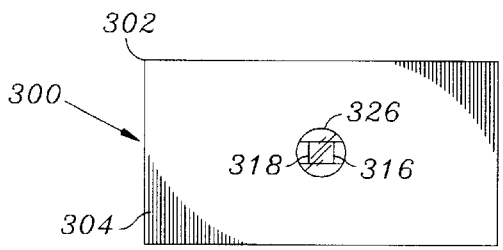
FIG. 9B is a drawing of the two-component chromatographic assay device of FIG. 9A shown with the two components having been brought into opposition.

FIG. 9B shows the device 300 when the first and second opposable components 302 and 304 are placed into opposition; the detection zone 316 and the control zone 318 are visible through the window 326 in the second opposable component 304.

In this device, the first application means can comprise a sample application pad and the second application means can comprise a buffer application pad to which buffer is added. The first application means (sample application pad) can contain at least one reagent for treatment of the sample before it is applied to the chromatographic medium, as described above. The second application means (buffer application pad) typically contains a specific binding partner for the analyte in a form that can be reconstituted by the addition of an aqueous liquid, as described above.

The chromatographic medium can include detection and control zones, as described above.

The sample application pad preferably further comprises an inert dye so that the flow of the sample through the chromatographic medium can be monitored visually. Preferably, the inert dye is of a contrasting color to that of the detectable label. For example, when the detectable label is pink colloidal gold, the inert dye can be blue.

The first application means can be placed into operable contact with the first end of the chromatographic medium by contacting the first application means with a conducting means that is itself in operable contact with the first end of the chromatographic medium.

In use, the sample to be tested is applied to the first application means (sample application pad) and a buffer solution is applied to the second application means (buffer application pad). The sample migrates across the chromatographic medium and passes the detection zone, where analyte binds the immobilized specific binding partner. The migration of sample is monitored by observing the inert dye. After the sample has migrated a sufficient distance, for example, two-thirds or three-fourths of the length of the chromatographic medium, the first and second opposable components are brought into opposition and the absorbent pad is brought into contact with the first application means. This reverses the flow of the sample along the chromatographic medium, allowing additional capture of the analyte. It also brings the second application means into contact with the conducting means and causes a buffer solution, containing resolubilized labelled specific binding partner to the analyte, to be applied to the chromatographic medium. The buffer solution migrates through the chromatographic medium from the second end of the chromatographic medium to the first end. When it reaches the detection zone, labelled specific binding partner to the analyte binds to the analyte already bound to the detection zone. Detection and/or determination of the analyte is then performed as described above.

Because the first and second opposable components are not in contact when the sample is applied as the first liquid to the first application means, it is possible to apply either the sample or the buffer to reconstitute the labelled specific binding partner first.

A variation of this bi-directional device replaces the conducting means on the first opposable component with a first absorbing means of finite capacity. The absorbing means on the second opposable component then is a second absorbing means. The absorbing means of finite capacity on the first opposable component has the property that liquid can be drawn back through it when the second application means is placed in operable contact with it and the second absorbing means is placed in operable contact with the first application means.

B. Two-Component Device with Cover

Another embodiment of a chromatographic assay device according to the present-invention is a two-component device with a cover.

Figure 10A:
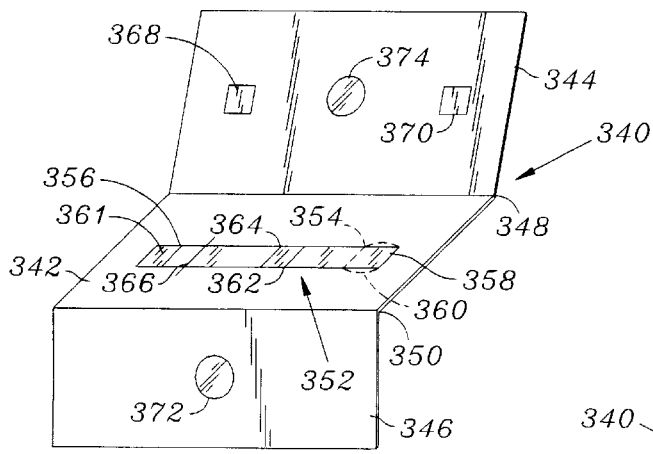
FIG. 10A is a drawing of yet another two-component assay device suitable for bi-directional chromatography, incorporating a cover.

This embodiment of the assay device is shown in FIG. 10A. The assay device 340 has a first opposable component 342, a second opposable component 344, and a cover 346. The second opposable component 344 is hingedly attached to one side of the first opposable component 342 by a first hinge 348. The cover 346 is hingedly attached to the opposite side of the first opposable component 342 at a second hinge 350. The first opposable component 342 has a chromatographic medium 352 having a first end 354 and a second end 356. Adjacent to and in operable contact with the first end 354 of the chromatographic medium 352 is a first application means or sample pad 358 which is located in a recess 360. A first absorbing means 361 is adjacent to and in operable contact with the second end 356 of the chromatographic medium. The chromatographic medium 352 contains a detection zone 362 and a control zone 364 and is optionally marked with a limit line 366. The limit line 366 can be optionally marked on the first opposable component 342 as well. The second opposable component 344 comprises a second application means 368 and a second absorbing means 370. The cover 346 contains a first aperture 372. Preferably, the second opposable component 344 contains a second aperture 374.

Figure 10B:
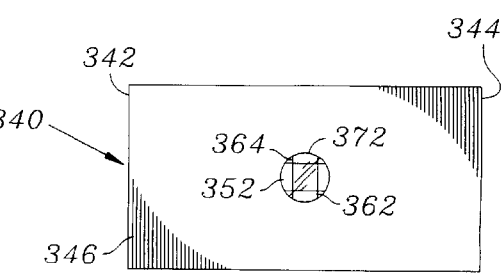
FIG. 10B is a drawing of the two-component chromatographic assay device of FIG. 10A shown with the two components having been brought into opposition.

FIG. 10B depicts this device 340 when the second opposable component 344 is folded over the first opposable component 342 and the cover 346 is folded over the second opposable component 344. A portion of the chromatographic medium 352 is visible through the first aperture 372 of the cover 346 and through the second aperture 374 of the second opposable component 344, including the detection zone 362 and the control zone 364.

In the operation of this device, the addition of a first liquid to the first application means causes the first liquid to be applied to the first end of the chromatographic medium. Typically, the first liquid is a sample that may contain an analyte.

In this device, the function of the recess in the first opposable component is to position the second absorbing means so that can be placed at least partially in direct contact with the chromatographic medium in order to remove excess sample, while keeping the first application means from blocking this contact. Were the recess not present, direct contact would be blocked by the first application means itself and removal of excess sample would be less efficient.

Bringing the first and second opposable components into opposition:

(1) causes the second application means to come into operable contact with the first absorbing means so as to apply the second liquid to the second end of the chromatographic medium; and (2) causes the second absorbing means to come into operable contact with the first application means so as to withdraw fluid from the chromatographic medium via the first application means.

This device is therefore useful for bi-directional chromatography.

The first application means can comprise a sample preparation means that can contain at least one reagent for treatment of the sample before it is applied to the chromatographic medium, as described above. The chromatographic medium can include detection and control zones, as described above.

The second opposable component and the cover can each have an aperture cut therein to permit viewing of at least a portion of the chromatographic medium where a first and second opposable components are opposed and the cover is folded over the first and second opposable components.

The first application means can also contain an inert dye to indicate the progress of chromatography as described above, and the chromatographic medium can contain a limit line to indicate the point at which the first and second opposable components should be brought into opposition.

The second application means typically contains a labelled specific binding partner for the analyte, as described above.

In use, the sample is added to the first application means so that chromatography can proceed in the chromatographic medium from the first end toward the second end. When the dye reaches the limit line, the first and second opposable components are brought into opposition, the contents of the second application means is applied to the first absorbing means, and the second absorbing means is placed in operable contact with the first application means. This reverses chromatographic flow and draws the labelled specific binding partner back through the chromatographic medium from the second end to the first end. The presence of analyte is indicated by the appearance of detectable label at the sample detection zone, while the appearance of detectable label at the control zone indicates the test was correctly performed.

The cover can be folded over the second opposable component to more securely lock and hold the second opposable component against the first opposable component. This allows more convenient storage of the device, after use, as in a medical record.

C. Three-Component Device

Another embodiment of a chromatographic assay device according to the present invention is a three-component assay device utilizing bi-directional chromatography.

This embodiment of the three-component assay device is shown in FIG. 11A. The assay device 400 has a first opposable component 402, a second opposable component 404, and a third opposable component 406. The second opposable component 404 is hingedly attached to one side of the first opposable component 402 by a first hinge 408; the third opposable component 406 is hingedly attached to the opposite side of the first opposable component 402 by a second hinge 410. The first opposable component 402 has a chromatographic medium 412 having a first end 414 and a second end 416. The chromatographic medium 412 has a detection zone 418 and a control zone 420. In operable contact with the first end 414 of the chromatographic medium 412 is a first conducting means 422 and in operable contact with the second end 416 of the chromatographic medium 412 is a second conducting means 424. The second opposable component 404 comprises a first absorbing means 426 and a first application means 428, intended for application of the sample. A first aperture 430 is cut in the second opposable component 404 to allow viewing of at least a portion of the chromatographic medium 412. The first aperture 430 is between the first absorbing means 426 and the first application means 428. The third opposable component 406 comprises a second application means 432 intended for a labelled secondary specific binding partner and a second absorbing means 434. A second aperture 436 is cut in the third opposable component 406 to allow viewing of at least a portion of the chromatographic medium 412. The second aperture 436 is between the second application means 432 and the second absorbing means 434. When the device 400 is closed, with the second opposable component 404 folded over the first opposable component 402 and the third opposable component 406 folded over the first opposable component 402, at least a portion of the chromatographic medium 412 is visible through the first aperture 430 and the second aperture 436 (FIG. 11B).

In this device, bringing the first and second opposable components into opposition causes the first absorbing means to come into operable contact with the second conducting means and causes the first application means to come into operable contact with the first conducting means to apply fluid to the chromatography medium, so that a first liquid applied to the first application means is drawn through at least a portion of the chromatographic medium.

The first and second opposable components are then withdrawn from opposition and the first and third opposable components are brought into opposition. This causes the second absorbing means to come into operable contact with the first conducting means to withdraw fluid from the chromatography medium and causes the second application means to come into operable contact with the second conducting means to apply fluid to the chromatography medium. This causes a reversal of flow so that a second liquid applied to the second application means is drawn through at least a portion of the chromatographic medium through which the first liquid has been drawn in the direction opposite to the direction in which the first liquid was drawn through the chromatographic medium. The first, second, and third opposable components are in such a configuration that, when the third opposable component is brought into opposition with the first opposable component, the second opposable component can be folded over the first and third opposable components to form a cover. Both the second and third opposable components contain apertures that allow viewing of at least a portion of the chromatographic medium.

In the performance of an assay using this device, firm pressure between the second absorbing means and the first conducting means is important to assure that non-specific IgG is withdrawn from the medium before the advancing front of anti-IgG label. If mixing occurs, the non-specific IgG neutralizes the conjugate leaving less/none available for labeling the specifically captured IgG. The third opposable component of the device helps keep consistent pressure applied to reliably effect this function. This is one of the advantages of assay devices according to the present invention.

Typically, the first application means contains a first specific binding partner for the analyte in a form that can be resolubilized by the application of an aqueous sample to the first application means. The first specific binding partner can be directly labelled with a detectable label. Alternatively, indirect labelling of the first specific binding partner can be used. Indirect labeling is particularly useful for testing for Giardia or other antigens for which commercially available antibodies are directly labelled only with difficulty. When the first specific binding partner is not directly labelled, the second application means preferably contains a labelled secondary specific binding partner for the first specific binding partner, as discussed below in Section II.

D. Multiplex Devices

Another embodiment of a chromatographic assay device according to the present invention is a multiplex assay device that can perform multiple assays simultaneously. The assays can be performed on the same analyte or different analytes. In general, all versions of the device described above are suitable for multiplex use by providing first and second opposable components, and third opposable components if necessary, with multiple chromatographic media, sample preparation means, application means, conducting means, absorbing means, and other required elements.

One version of a multiplex assay device according to the present invention is shown in FIG. 12. The assay device 460 has a first opposable component 462 and a second opposable component 464. The second opposable component 464 is hingedly attached to the first opposable component 462 by a hinge 466. The first opposable component 462 comprises a plurality of chromatographic media 468. Each of the chromatographic media 468 has a first end 470 and a second end 472, and comprises a detection zone 474 and a control zone 476. The second end 472 of each chromatographic medium 468 is operably connected to a conducting means 478. There is a separate conducting means 478 for each chromatographic medium 468. The second opposable component 464 comprises a plurality of sample preparation means 480, one for each chromatographic medium 468. Bringing the first and second opposable components 462 and 464 into opposition causes each of the application means 480 to be applied to the corresponding chromatographic medium 468. The second opposable component 464 contains a plurality of apertures 482, one for each chromatographic medium 468.

In this device, the first and second opposable components can be brought into opposition so as to cause each sample preparation means to apply each sample to be tested to the corresponding chromatographic medium. Typically, each sample preparation means contains labelled specific binding partner for the analyte to be tested in a form that can be resolubilized by the addition of a liquid sample to the sample preparation means. Alternatively, the labelled specific binding partner in a liquid form can be added to the sample preparation means before or after the addition of the sample thereto.

Each of the chromatographic media that comprise the device preferably contains a detection zone and control zone, as described above.

This multiplex device can contain from 2 to 12 or more sample preparation means and chromatographic media, depending upon the assay for which the device is to be employed. Typically, the device contains from 2 to 5 separate sample preparation means and chromatographic media.

This embodiment of the device can be used to assay a number of different analytes in different aliquots of the same sample, or can be used to assay the same analyte in a number of different samples. This latter mode is particularly useful in assaying for a condition for which samples taken at different times from the same patient must be assayed for the analyte of interest, such as fecal occult blood. The presence of fecal occult blood is frequently determined by means of a series of stool samples taken once a day or at other intervals for a prescribed period. Alternatively, one or more of the assays can be used for controls or reference standards.

A number of variations of this multiplex device are possible. In one variation, the second opposable component further comprises a conducting means in operable contact with the second end of each chromatographic medium.

In yet another variation of the multiplex device, at least one sample preparation means could comprise a collapsible well, to which an extraction swab or other sample-containing device can be added. In this variation, the first opposable component can further comprise hingedly foldable wings that fold over the second opposable component when the first opposable component and second opposable component are brought into opposition.

This variation of the multiplex device is shown in FIG. 13. The device 500 has a first opposable component 502 and a second opposable component 504. The second opposable component 504 is hingedly attached to the first opposable component 502 by a hinge 506. Hingedly attached to the first opposable component 502 are two foldable wings 508 and 510. The first opposable component 502 has a control well 512 and a collapsible sample well 514, i.e., made of a sponge-like material. The second opposable component 504 has a plurality of chromatographic media 516, in this example, two, each with a detection zone 518 and a control zone 520. The second opposable component has an aperture 522 for viewing of a portion of the chromatographic media 516, including the detection zone 518 and the control zone 520. When the first opposable component 502 and second opposable component 504 are opposed, samples in the control well 512 and the collapsible sample well 514 are applied to the corresponding chromatographic media 516 for chromatography.

Yet another variation of the multiplex device is particularly useful for determination of hemoglobin in fecal occult blood. This device is adapted to receive a test card that includes several dried fecal samples, typically taken on consecutive days.

Figure 14:
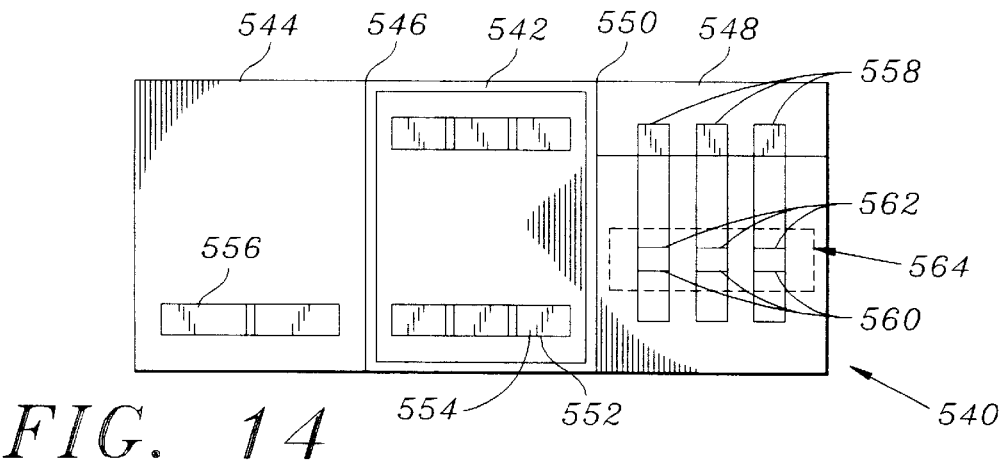
FIG. 14 is a drawing of yet another version of a multiplex assay device according to the present invention adapted to receive a test card.

This device is shown in FIG. 14. The assay device 540 comprises a first opposable component 542, a second opposable component 544 hingedly attached to the first opposable component 542 by a first hinge 546, and a third opposable component 548 hingedly attached to the first opposable component 542 by a second hinge 550. The first opposable component 542 is adapted to receive a test card 552 that has a plurality of dried specimens 554 mounted thereon. The second opposable component 544 has a reagent pad 556 incorporated therein. The third opposable component 548 has a plurality of chromatographic media 558 each with a detection zone 560 and control zone 562. There is a separate chromatographic medium 558 for each sample to be tested. The third opposable component 548 has an aperture 564 to permit viewing of at least a portion of the chromatographic media 558, including each detection zone 560 and control zone 562. In use, the second opposable component 544 is folded over the first opposable component 542 after adding reagents to reagent pad 556 of the second opposable component 544. The second opposable component 544 is then unfolded from the first opposable component 542; finally, the third opposable component 548 is folded over the second opposable component 544 to apply the contents of the reagent pad 556 and sample to the chromatographic media 558.

In this device, the reagent pad comprises a specific binding partner for the analyte labelled with a detectable label in a form that can be resolubilized by the addition of an aqueous reagent to the reagent pad. The reagent added is an extraction reagent for the analyte to be assayed, such as hemoglobin.

When the second opposable component is opposed to the first opposable component, the analyte is extracted from the samples on the test card and binds to the labelled specific binding partner. When the third opposable component is subsequently opposed to the second opposable component, any analyte bound to the labelled specific binding partner migrates through the chromatography medium, and binds to the detection zone in the medium. This detection zone contains a second specific binding partner for the analyte as described above. Each chromatographic medium can contain a control zone as described above to ensure accurate performance of the assay.

Yet another variation of a multiplex device according to the present invention is a multiplex device similar to that shown in FIG. 12, but adapted to receive a test card. The test card can contain a plurality of samples, such as dried fecal samples when a fecal occult blood test is performed.

Figure 15:
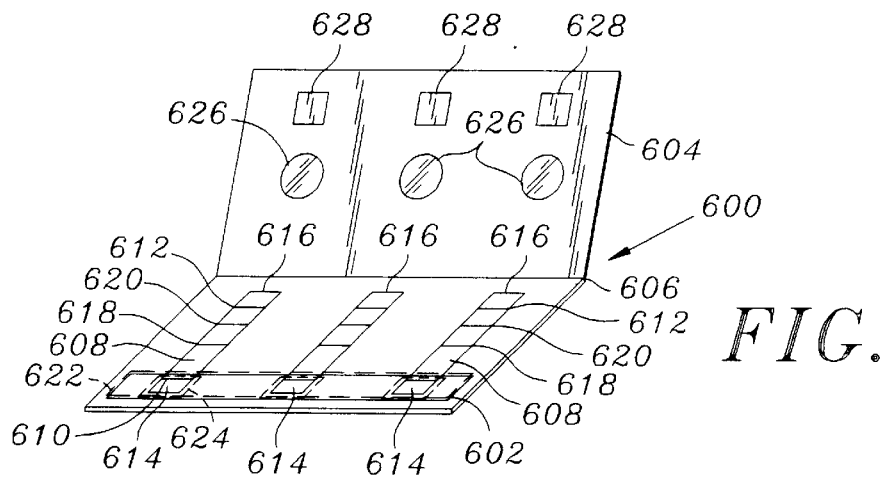
FIG. 15 is a drawing of yet another version of a multiplex assay device according to the present invention adapted to receive a test card.

This variation is shown in FIG. 15. The assay device 600 has a first opposable component 602 and a second opposable component 604. The second opposable component 604 is hingedly attached to the first opposable component 602 by a hinge 606. The first opposable component 602 comprises a plurality of chromatographic media 608. Each of the chromatographic media 608 has a first end 610 and a second end 612, and comprises a detection zone 618 and a control zone 620. The first end 610 of each chromatographic medium 608 is in operable contact with a conducting means 614, and the second end 610 of each chromatographic medium 608 in operable contact with an absorbing means 616. There is a separate conducting means 614 and absorbing means 616 for each chromatographic medium 608. The first opposable component 602 is adapted to receive a test card 622 containing a plurality of dried specimens 624 positioned so that they are in operable contact with each conducting means 614. The second opposable component 604 comprises a plurality of application means 628, one for each chromatographic medium 608. Preferably, each application means 628 contains labeled specific binding partner for the analyte in resolubilizable form.

In use, a buffer or other aqueous liquid is applied to each application means 628 to reconstitute the labeled specific binding partner. Bringing the first and second opposable components 602 and 604 into opposition causes each of the application means 628 to be applied to the corresponding dried specimen 624 so that the contents of each dried specimen 624 and each application means 628 are applied to each conducting means 614, and thus to each chromatographic means 608. The second opposable component 604 contains a plurality of apertures 626, one for each chromatographic medium 608, for viewing of each chromatographic medium 608.

II. Analytes and Antibodies for use with the Assay Device

The analytes suitable for detection with an assay device according to the present invention include antigens, haptens, and antibodies. Antigens detectable with the device include hemoglobin, Streptococcus A and B antigens, antigens specific for the protozoan parasite Giardia, and viral antigens, including antigens specific for HIV and the Australia antigen specific for hepatitis. Antibodies that can be assayed include antibodies to bacteria such as *Helicobacter pylori* and to viruses, including HIV.

If the analyte is a hapten or antigen, the first and second specific binding partners are preferably antibodies. In many applications, it is preferable that the first and second specific binding partners are antibodies to different epitopes on the analyte, but this is not required. The antibodies can be polyclonal or monoclonal, and can be IgG, IgM or IgA. In many applications, polyclonal antibodies are preferred, as their natural variability may allow more accurate detection in systems where antigenic polymorphisms exist or may exist.

When the analyte is a hapten, it is strongly preferred that the first and second specific binding partners be antibodies to different epitopes; otherwise, there may be an undesirable competition reaction set up that may interfere with binding of the complex of the labelled specific binding partner and the analyte to the immobilized second specific binding partner.

Where the analyte is an antibody, the first specific binding partner is typically a labelled antibody that binds to the analyte on the basis of species, class, or subclass (isotype) specificity. It is highly preferred that the first specific binding partner to an antibody analyte binds to the constant region of the antibody analyte, in order to prevent interference. When the analyte is antibody, the second specific binding partner is preferably an antigen or hapten for which the antibody analyte is specific.

In some applications, it is desirable to employ indirect labelling. For example, in testing for Giardia antigen, an IgM antibody can be used that may be difficult to label directly. In that case, a secondary specific binding partner specific for the mobile first specific binding partner can be labelled. Typically, the labelled secondary specific binding partner binds to the antibody that is the first specific binding partner on the basis of species, class, or subclass specificity.

As an alternative to the use of a secondary specific binding partner, the first specific binding partner can be conjugated to biotin and an avidin-conjugated label can be used.

These relationships between analytes, specific binding partners, and labels are summarized in Table 1 below.

The invention is illustrated by the following Examples. The Examples are for illustrative purposes only and are not to be construed as limiting the scope of the invention in any manner.

EXAMPLES

Example 1

Construction of Device for Detecting Streptococcal Antigen

TABLE I

SCHEMES OF BINDING

| ANALYTE | 1ST SBP (MOBILE) | 2ND SBP (FIXED) | SECONDARY SBP | COMPLEX FORMED |
|---------|------------------|-----------------|---------------|----------------|
| Ag | $Ab_1*$ | $Ab_2$ | — | $Ab_2$—Ag—$Ab_1*$ |
| H | $Ab_1*$ | $Ab_2$ | — | $Ab_2$—H—$Ab_1*^{(1)}$ |
| Ab | $Ab_c*$ | Ag | — | Ag—Ab—$Ab_c*$ |
| Ag | $Ab_1$ | $Ab_2$ | $Ab_c*$ | $Ab_2$—Ag—$Ab_1$—$Ab_c*$ |
| Ab | $Ab_{c1}$ | Ag | $Ab_{c2}*$ | Ag—Ab—$Ab_{c1}$—$Ab_{c2}*$ |
| Ag | $Ab_1$—Bi | $Ab_2$ | Av—L | $Ab_2$—Ag—$Ab_1$—Bi—Av—L |

Ag = Antigen
H = Hapten
$Ab_1$ = 1st Antibody
$Ab_2$ = 2nd Antibody
$Ab_c$, $Ab_{c1}$, $Ab_{c2}$ = Antibody specific for another antibody
Bi = Biotin
Av = Avidin
L = Label
*Indicates labelled component
$^{(1)}Ab_2$ and $Ab_1*$ preferred to bind to different epitopes Chromatographic assay devices according to the present invention can readily be adapted for the performance of competitive immunoassays for analytes that bind antibodies in a monovalent manner, such as drugs and other haptens. In such competitive immunoassays, the labeled conjugate is an antibody-label conjugate and the detection zone comprises immobilized analyte analogue. The antibody-label conjugate is present along with a quantity of unlabeled antibody sufficient to prevent binding of the antibody-label conjugate to the immobilized analyte analogue in the absence of analyte in the test sample.

III. Test Kits

Another aspect of the present invention is test kits that can be used to detect particular analytes. A test kit comprises:

(1) a chromatographic assay device according to the present invention;

(2) any necessary reagents required to treat or extract the sample; and (3) optionally, if the assay device does not incorporate a labelled specific binding partner to the analyte in a form that can be resolubilized, the required specific binding partner.

The components required in (2) and (3) are packaged separately and can be in liquid or solid form (freeze-dried, crystallized, precipitated, or aggregated). If the latter, they are resolubilized by the user, typically with distilled or purified water, with physiological saline, or a buffer solution.

Still other variations of test devices according to the present invention are possible. For example, any of the two-component devices described can have a cover hingedly attached to one of the opposable components. This cover can have an aperture cut therein to allow viewing of at least a portion of the chromatographic medium.

A device was constructed for detecting Streptococcus A antigen using labelled antibody to Streptococcus A antigen. The device was constructed essentially as depicted in FIG. 16.

Figure 16:
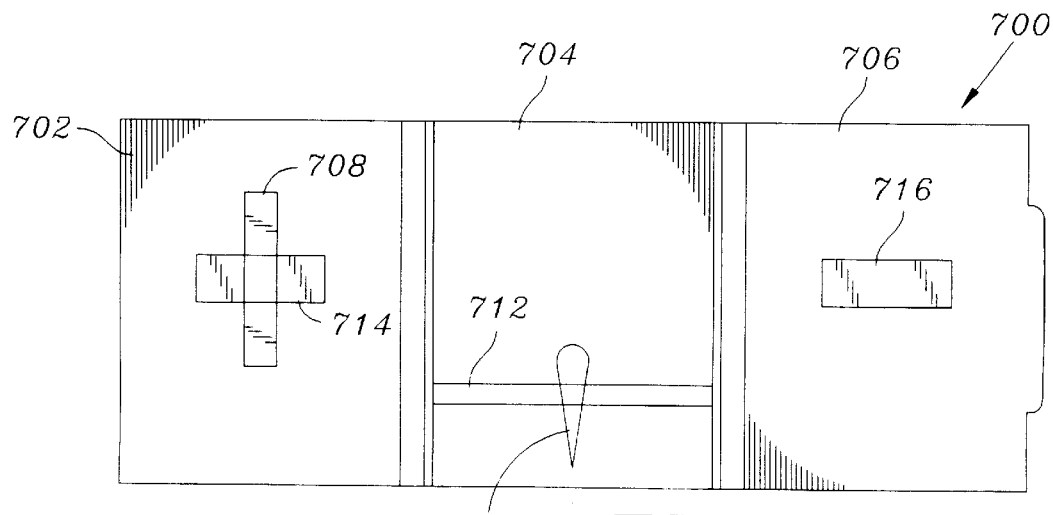
FIG. 16 is a depiction of an assay device according to the present invention suitable for receiving a swab or similar sampling device and designed for detection of Streptococcus A antigen.

FIG. 16 shows a chromatographic assay device 700 according to the present invention with a first opposable component 702, a second opposable component 704 hingedly attached to the first opposable component 702, and a cover 706 hingedly attached to the second opposable component 704. The first opposable component 702 includes a chromatographic medium 708. The second opposable component 704 includes a teardrop-shaped well 710 held in place by a ribbon 712. The first opposable component 702 contains a first window 714 and the cover contains a second window 716.

The opposable components were made of a hard, impervious plastic such as Lexan®. The first and second opposable components, as well as the cover, each were about 3" in length; the first opposable component was about 2.25" in width, while the second opposable component and the cover was each about 2.375" in width. The second opposable component was lined with foam rubber, into which a teardrop-shaped well was cut to accept a swab or other sampling device. The swab was held in place with a ribbon separately inserted into the second opposable component across the well.

The chromatographic medium was a nitrocellulose strip 8 $\mu$m thick and 0.5" in length, (MSI, Westborough, Mass.), affixed to the plastic backing by means of double-sided tape (3M, Minneapolis, Minn.). The conducting means and absorbing means were cellulose strips (Ahlstrom Filtration, Holly Springs, Pa.), 17/32" in length for the absorbing means, which was Ahlstrom Grade 939, and 0.25" in length for the conducting means, which was Ahlstrom Grade 1281. The detector application pad was also Ahlstrom Grade 1281, and was 0.375" wide. The detector application pad overlapped slightly with the conducting means, which in turn overlapped slightly with the chromatographic medium at its first end. The chromatographic medium overlapped slightly at its second end with the absorbing means.

The required reagents were first incorporated in the chromatographic medium and the detector application pad, after which the device was assembled using double-sided tape to hold the components to the backing.

The detection zone comprised rabbit anti-Streptococcus A antibody at 2 mg/ml in 0.001 mole/l phosphate buffered saline, pH 7.2. The control zone comprised goat anti-rabbit IgG at a similar concentration in the same buffer. The antibody solutions were applied to the appropriate regions of the chromatographic medium and dried at 100° F. in a low humidity environment. The chromatographic medium was wet in excess blocking solution (Blocking Reagent for ELISA, Boehringer Mannheim, Mannheim, Germany, diluted 1:10 with distilled water containing 0.2% Tween 20) and again dried at 100° F.

The detector application pad contained rabbit anti-Streptococcus antibody labelled with 40-nm colloidal gold particles. To apply the labelled antibody to the detector application pad, the labelled antibody was diluted 1:1.5 with DBN (1.5 mole/l Tris-HCl, pH 7.4, 1% (v/v) Tween 20, 0.4% (v/v) Brij 35, 0.02% (w/v) sodium azide, 3 mg/ml rabbit IgG). Per test, 15 $\mu$l of diluted labelled antibody was added to the detector application pad. The detector application pad was dried for 30 minutes at 100° F.

Example 2
Detection of Streptococcal Antigen Using Device of Example 1

The device of Example 1 was used to detect Streptococcus A antigen. A woven dacron swab to which varying quantities of Streptococcus type A bacteria had been added was inserted into the sample well. Three drops of Extraction Reagent A (0.25% acetic acid, 5% Tween 20), and three drops of Extraction Reagent B (2 mole/l sodium nitrite, 5% Tween 20) were added to the swab, mixed by gently rotating the swab, and incubated for one minute. The device was then closed, so that the first and second opposable components were brought into contact, and the cover was then folded over the first opposable component. The result was read after an incubation period of from 2 minutes to 5 minutes. The development of a pink-red band in the detection zone of the chromatographic medium indicated the detection of Streptococcus A antigen.

The device of Example 1 could detect $1\times10^5$ Streptococcus A organisms after a 2-minute incubation, and could detect $5\times10^4$ Streptococcus A organisms after a 5-minute incubation. For a comparison, the Concise™ immunoassay of Hybritech (La Jolla, Calif.) could detect $1\times10^5$ Streptococcus A organisms only after a 5-minute incubation, and could not detect $5\times10^4$ Streptococcus A organisms even after a 20-minute incubation. Similarly,-the Smart™ immunoassay of New Horizons could detect $1\times10^5$ Streptococcus A organisms only after a 7-minute incubation, and gave an equivocal result with $5\times10^4$ Streptococcus A organisms after a 7-minute incubation.

Example 3
Device for Detecting Hemoglobin in Fecal Occult Blood

Prospective Example

An assay device for the detection of hemoglobin in fecal occult blood is constructed according to FIGS. 1A and 1B, incorporating the optional conducting means at the first end of the chromatographic medium. A labeled specific binding partner is applied to the sample application pad in resolubilizable form. The labeled specific binding partner is goat anti-human hemoglobin antibody labeled with colloidal gold. A fecal sample of 60 $\mu$l is applied to the sample application pad and allowed to mix with conjugate. The device is closed and the combination of the fecal sample and reconstituted antibody contacts the conducting means and moves through the chromatographic medium. Chromatography is allowed to proceed for a period of about 1 minute to about 5 minutes. The chromatographic medium contains a detection zone of immobilized anti-human Hb antibody, and a control zone of immobilized rabbit anti-goat IgG antibody. Color appearing at both the detection zone and the control zone indicates a positive result, i.e., the presence of occult blood in the fecal sample. Color appearing at the control zone, but not at the detection zone, indicates the absence of occult blood and the correct performance of the test.

This device is capable of detecting hemoglobin in fecal occult blood in a concentration range of from about 0.2 ml blood/100 g feces to about 17 ml blood/100 g feces. This device is free from interference caused by peroxidase and dietary (non-human) hemoglobin.

Advantages of the Invention

Chromatographic assay devices according to the present invention allow the rapid and accurate detection of clinically important analytes, such as Streptococcus A and B antigen, hemoglobin for the determination of fecal occult blood, and antibody to *Helicobacter pylori*. The construction of the devices allows more even application of the samples to the chromatographic medium, and reduces interference that might otherwise be introduced by particulates or colored samples. The use of colloidal metal labels in a resolubilizible form provides extremely rapid kinetics of labeling and allows substantially complete formation of binary analyte-label complexes before the sample is applied to the chromatographic medium. This aids in the separation of contaminants and improves the performance of the assay. Additionally, the construction and arrangement of the housing of the device aids in the performance of the assay by assuring the withdrawal of excess immunoglobulin-containing sample that could otherwise create interference.

Extraction of biological samples such as blood, sputum, or feces can be performed directly in the devices, reducing the quantity of contaminated material that must be disposed and reducing the likelihood of accidental infection of physicians, technicians, or the public by such contaminated material. Additionally, the devices are capable of performing bi-directional chromatography to further increase accuracy and reduce interference. Test methods using devices according to the present invention have a wide dynamic range and are substantially free from false negatives that may occur in other test methods at high concentrations of analyte.

Although the present invention has been described with considerable detail, with reference to certain preferred versions thereof, other versions and embodiments are possible. These versions include other arrangements of two- or three-component devices that operate by the basic principles described herein and utilize any of: (a) in situ extraction of samples; (b) resolubilization of a labeled specific binding partner and rapid binding to analyte; and (c) arrangement of the chromatographic medium and absorbing means to remove excess sample that could otherwise create interference. These versions include assay devices adapted for competitive immunoassays. Therefore, the scope of the invention is determined by the following claims.

I claim:

1. A chromatographic assay device for detection or determination of an analyte comprising:
    (a) an opposable component including a sample preparation means for receiving a sample to be assayed;
    (b) a second opposable component including a chromatographic medium;
    wherein the first and second opposable components are brought into opposition so as to cause the sample preparation means to apply the sample to be tested to the chromatographic medium so that the analyte is detected by a labeled second specific binding partner bound to the analyte, the analyte in turn being directly bound to a first specific binding partner bound to the chromatographic medium so that the labeled second specific binding partner is indirectly bound to the first specific binding partner through the analyte, the labeled second specific binding partner either being present in the assay device in either the first or second opposable components prior to the initiation of an assay or being added to the assay device during the performance of the assay.

2. A chromatographic assay device for detection or determination of an analyte comprising:
    (a) a first opposable component including a sample preparation means for receiving a sample to be assayed; and
    (b) a second opposable component including a chromatographic medium, the chromatographic medium further including a detection zone smaller than the chromatographic medium;
    wherein the first and second opposable components are brought into opposition so as to cause the sample preparation means to apply the sample to be tested to the chromatographic medium;
    wherein the detection zone contains a first specific binding partner to the analyte immobilized therein so that the analyte is detected by a labeled second specific binding partner to be bound to the analyte, the analyte being in turn directly bound to the first specific binding partner, the labeled second specific binding partner being indirectly bound to the first specific binding partner through the analyte, the labeled second specific binding partner either being present in either the first or second opposable component of the device prior to the initiation of an assay or being added to the assay device during the performance of the assay.

3. The chromatographic assay device of claim 2 wherein the analyte is an antigen or hapten and the first specific binding partner is an antibody to the antigen or hapten.

4. The chromatographic assay device of claim 2 wherein the analyte is an antibody and the first specific binding partner is a hapten or antigen bound specifically by the antibody.

5. A chromatographic assay device for detection or determination of an analyte comprising:
    (a) a first opposable component including:
        (i) a chromatographic medium having first and second ends;
        (ii) a conducting means in operable contact with the first end of the chromatographic medium; and
        (iii) an absorbing means in operable contact with the second end of the chromatographic medium; and
    (b) a second opposable component including:
        (i) a first application means that is a sample application pad; and
        (ii) a second application means that is a detector application pad to which detecting reagent is applied;
        the first and second application means being positioned on the second opposable component such that they are not in operable contact when the first and second opposable components are not in opposition;
    wherein bringing the first and second opposable components into opposition places the conducting means in operable contact with the first application means and places the conducting means in operable contact with the second application means, thereby placing the first and second application means in operable contact with each other and applying the contents of the sample application pad and the detector application pad to the conducting means, and wherein the conducting means transfers the contents of the sample application pad and the detector application pad to the first end of the chromatographic medium of the first opposable component;
    wherein the detector application pad contains a first specific binding partner to the analyte in a form that is resolubilized by addition of an aqueous liquid to the detector application pad, the first specific binding partner being labeled with a detectable label, and the chromatographic medium further comprises a detection zone smaller in area than the chromatographic medium, the detection zone containing a second specific binding partner to the analyte immobilized thereto, such that a ternary complex comprising the first specific binding partner, the analyte, and the second specific binding partner forms at the detection zone if analyte is present in the sample, the second specific binding partner being bound directly to the analyte and the labeled first specific binding partner being bound indirectly to the second specific binding partner through the analyte.

6. The chromatographic assay device of claim 5 wherein the detectable label is a visually detectable label.

7. A test kit for the detection or determination of an analyte comprising:
    (a) the chromatographic assay device of claim 5; and
    (b) an aqueous liquid for resolubilizing the specific binding partner for the analyte labeled with a detectable label, to be applied to the detector application pad.

8. A method of detection or determination of an analyte in a test sample comprising the steps of:
    (a) applying the sample to the first application means of the chromatographic assay device of claim 5;
    (b) bringing the first and second opposable components of the chromatographic assay device into opposition, such that the sample comprises the aqueous liquid resolubilizing the specific binding partner in the detector application pad, and such that the sample and the resolubilized labeled specific binding partner are applied to the first end of the chromatographic medium;
    (c) allowing the sample and the labeled specific binding partner to move through at least a portion of the chromatographic medium, the portion including the detection zone, so that the detection reagent gives a detectable indication of the presence or quantity of the analyte; and
    (d) observing or measuring the detection reagent at the detection zone in order to detect or determine the analyte.

9. A chromatographic assay device for the detection or determination of an analyte comprising:
   (a) a first opposable component including:
      (i) a chromatographic medium having first and second ends;
      (ii) a conducting means in operable contact with the first end of the chromatographic medium;
      (iii) an absorbing means in operable contact with the second end of the chromatographic medium; and
      (iv) a detector application pad in direct contact with the conducting means and positioned such that it is in indirect contact with the first end of the chromatographic medium; and
   (b) a second opposable component that is a sample application pad;
      wherein bringing the first and second opposable components into opposition causes the sample application pad to apply a sample to be tested to the detector application pad and thus to the first end of the chromatographic medium through the conducting means;
      wherein the detector application pad contains a first specific binding partner to the analyte in a form that is resolubilized by addition of an aqueous liquid to the detector application pad, the first binding partner being labeled with a detectable label, and the chromatographic medium further includes a detection zone smaller than the chromatographic medium, the detection zone containing a specific binding partner to the analyte immobilized thereto, such that a try complex comprising the first specific binding partner, the analyte, and the second specific binding partner forms at the detection zone if analyte is present in the sample, the labeled first specific binding partner being indirectly bound to the immobilized second specific binding partner through the analyte in the ternary complex.

10. The chromatographic assay device of claim 9 wherein the contents of the sample application pad after a sample is applied thereto comprise an aqueous liquid, and the aqueous liquid applied to the detector application pad comprises the contents of the sample application pad.

11. A test kit for the detection or determination of an analyte comprising:
   (a) the chromatographic assay device of claim 9; and
   (b) a specific binding partner for the analyte labelled with a detectable label, to be applied to the second application means.

12. A method for the detection or determination of an analyte in a test sample comprising the steps of:
   (a) applying the sample to the sample application pad of the chromatographic assay device of claim 9;
   (b) bringing the first and second opposable components of the chromatographic assay device into opposition, such that the sample comprises the aqueous liquid resolubilizing the specific binding partner in the detector application pad and such that the sample and the resolubilized labeled specific binding partner are applied to the first end of the chromatographic medium;
   (c) allowing the sample and the labeled specific binding partner to move through at least a portion of the chromatographic medium, the portion including the detection zone, so that the labeled specific binding partner gives a detectable indication of the presence or quantity of the analyte; and
   (d) observing or measuring the labeled specific binding partner at the detection zone in order to detect or determine the analyte.

13. A chromatographic assay device for the detection or determination of an analyte comprising:
   (a) a first opposable component including:
      (i) a chromatographic medium having first and second ends;
      (ii) an absorbing means in operable contact with the second end of the chromatographic medium; and
      (iii) a detector application pad in direct contact with the first end of the chromatographic medium;
   (b) a second opposable component including a sample application pad;
      wherein, where the first and second opposable components are brought into opposition, the detector application pad and the sample application pad are in contact except for a region of the sample application pad directly adjacent to the first end of the chromatographic medium, and whereby bringing the first and second opposable components into opposition causes the sample application pad to apply the sample to be tested to the detector application pad and thus the first end of the chromatographic medium;
      wherein the detector application pad contains a first specific binding partner to the analyte in a form that is resolubilized by addition of an aqueous liquid to the detector application, the first specific binding partner being labeled with a detectable label, and the detection zone is smaller in area than the chromatographic medium, the detection zone containing a second specific binding partner to the analyte immobilize thereto, such that a ternary complex comprising the first specific binding partner, the analyte, and the second specific binding partner forms at the detection zone if the analyte is present in the sample.

14. The chromatographic assay device of claim 13 wherein the contents of the sample application pad after a sample is applied thereto comprise an aqueous liquid, and the aqueous liquid applied to the detector application pad comprises the contents of the sample application pad.

15. A method for the detection or determination of an analyte in a test sample comprising the steps of:
   (a) applying the sample to the sample application pad of the chromatographic assay device of claim 14;
   (b) bringing the first and second opposable components of the chromatographic assay device into opposition, such that the sample comprises the aqueous liquid resolubilizing the specific binding partner in the detector application pad, and such that the sample and the resolubilized labelled specific partner are applied to the first end of the chromatographic medium;
   (c) allowing the sample and the labelled specific binding partner to move through at least a portion of the chromatographic medium, the portion including the detection zone, so that the labeled specific binding partner gives a detectable indication of the presence or quantity of the analyte; and
   (d) observing or measuring the labeled specific binding partner at the detection zone in order to detect the analyte.

* * * * *